US010144970B2

(12) United States Patent
Samowitz et al.

(10) Patent No.: US 10,144,970 B2
(45) Date of Patent: Dec. 4, 2018

(54) METHODS AND COMPOSITIONS RELATED TO A BRAF MUTATION AND MICROSATELLITE STABILITY

(75) Inventors: Wade S. Samowitz, Salt Lake City, UT (US); Martha L. Slattery, Salt Lake City, UT (US); Roger K. Wolff, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 786 days.

(21) Appl. No.: 11/995,647

(22) PCT Filed: Jul. 13, 2006

(86) PCT No.: PCT/US2006/027130
§ 371 (c)(1),
(2), (4) Date: Jan. 9, 2009

(87) PCT Pub. No.: WO2007/009013
PCT Pub. Date: Jan. 18, 2007

(65) Prior Publication Data
US 2009/0181371 A1 Jul. 16, 2009

Related U.S. Application Data

(60) Provisional application No. 60/699,011, filed on Jul. 13, 2005.

(51) Int. Cl.
*C12Q 1/68* (2018.01)
*C12P 19/34* (2006.01)
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/154* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 5,541,308 A * | 7/1996 | Hogan | C12Q 1/6811 435/6.12 |
|---|---|---|---|
| 2005/0048533 A1 * | 3/2005 | Sidransky | C12Q 1/6886 435/6.14 |
| 2007/0020657 A1 * | 1/2007 | Grebe | C12Q 1/6886 435/6.16 |

FOREIGN PATENT DOCUMENTS

WO  WO 05/047542  5/2005

OTHER PUBLICATIONS

Soares et al, Oncogene, 2003, vol. 22, pp. 4578-4580.*
Gryfe (NEMJ, 2000, 342:69-77).*
Wilhelm (Cancer Res, 2004, 64:7009-7109).*
Benson (J Clin Oncology, 2004, vol. 22, pp. 3408-3419).*
Juppner (Bone, (1995), vol. 17, No. 2, 39S-42S.*
Hegele, Arterioscler. Throm. Vasc. Biol., 2002, 22: 1058-1061.*
Langer et al. Nature, vol. 392(6679 Suppl.), pp. 5-10, 1998.*
Ioannidis, PLoS Med, 2005, 2(8): e124, 696-701.*
Buck et al (Biotechniques (1999) 27(3):528-536).*
Aaltonen LA, Peltomäki P, Leach FS, Sistonen P, Pylkkänen L, Mecklin JP, Järvinen H, Powell SM, Jen J, Hamilton SR, et al. (1993) Clues to the pathogenesis of familial colorectal cancer. Science. 260(5109): 812-816.
Begum S, Rosenbaum E, Henrique R, Cohen Y, Sidransky D, Westra WH. (2004) BRAF mutations in anaplastic thyroid carcinoma: implications for tumor origin, diagnosis and treatment. Mod Pathol. 17(11): 1359-1363.
Bertario L, Russo A, Sala P, Eboli M, Radice P, Presciuttini S, Andreola S, Rodriguez-Bigas MA, Pizzetti P, Spinelli P. (1999) Survival of patients with hereditary colorectal cancer: comparison of HNPCC and colorectal cancer in FAP patients with sporadic colorectal cancer. Int J Cancer. 80(2): 183-187.
Bild AH, Yao G, Chang JT, Wang Q, Potti A, Chasse D, Joshi MB, Harpole D, Lancaster JM, Berchuck A, Olson JA Jr, Marks JR, Dressman HK, West M, Nevins JR. (2006) Oncogenic pathway signatures in human cancers as a guide to targeted therapies. Nature. 439(7074): 353-357.
Boland CR, Ricciardiello L. (1999) How many mutations does it take to make a tumor? Proc Natl Acad Sci USA. 96(26): 14675-14677.
Boland CR, Thibodeau SN, Hamilton SR, Sidransky D, Eshleman JR, Burt RW, Meltzer SJ, Rodriguez-Bigas MA, Fodde R, Ranzani GN, Srivastava S. (1998) A National Cancer Institute Workshop on Microsatellite Instability for cancer detection and familial predisposition: development of international criteria for the determination of microsatellite instability in colorectal cancer. Cancer Res. 58(22): 5248-5257.
Bronner CE, Baker SM, Morrison PT, Warren G, Smith LG, Lescoe MK, Kane M, Earabino C, Lipford J, Lindblom A, et al. (1994) Mutation in the DNA mismatch repair gene homologue hMLH1 is associated with hereditary non-polyposis colon cancer. Nature. 368(6468): 258-261.
Chang DZ, Panageas KS, Osman I, Polsky D, Busam K, Chapman PB. (2004) Clinical significance of BRAF mutations in metastatic melanoma. J Transl Med. 2(1): 46.
Chong JM, Fukayama M, Hayashi Y, Takizawa T, Koike M, Konishi M, Kikuchi-Yanoshita R, Miyaki M. (1994) Microsatellite instability in the progression of gastric carcinoma. Cancer Res. 54(17): 4595-4597.
Davies H, Bignell GR, Cox C, Stephens P, Edkins S, Clegg S, Teague J, Woffendin H, Garnett MJ, Bottomley W, Davis N, Dicks E, Ewing R, Floyd Y, Gray K, Hall S, Hawes R, Hughes J, Kosmidou V, Menzies A, Mould C, Parker A, Stevens C, Watt S, Hooper S, Wilson R, Jayatilake H, Gusterson BA, Cooper C, Shipley J, Hargrave D, Pritchard-Jones K, Maitland N, Chenevix-Trench G, Riggins GJ, Bigner DD, Palmieri G, Cossu A, Flanagan A, Nicholson A, Ho JW, Leung SY, Yuen ST, Weber BL, Seigler HF, Darrow TL, Paterson H, Marais R, Marshall CJ, Wooster R, Stratton MR, Futreal PA. (2002) Mutations of the BRAF gene in human cancer. Nature. 417(6892): 949-954.
Deng G, Bell I, Crawley S, Gum J, Terdiman JP, Allen BA, Truta B, Sleisenger MH, Kim YS. (2004) BRAF mutation is frequently present in sporadic colorectal cancer with methylated hMLH1, but not in hereditary nonpolyposis colorectal cancer. Clin Cancer Res. 10(1 Pt 1): 191-195.

(Continued)

Primary Examiner — Sarae L Bausch
(74) Attorney, Agent, or Firm — Ballard Spahr LLP

(57) ABSTRACT

Disclosed are methods and compositions related to a BRAF mutation and microsatellite stability.

6 Claims, 4 Drawing Sheets
Specification includes a Sequence Listing.

(56) References Cited

OTHER PUBLICATIONS

Elsaleh H, Powell B, McCaul K, Grieu F, Grant R, Joseph D, Iacopetta B. (2001) P53 alteration and microsatellite instability have predictive value for survival benefit from chemotherapy in stage III colorectal carcinoma. Clin Cancer Res. 7(5): 1343-1349.
Fishel R, Lescoe MK, Rao MR, Copeland NG, Jenkins NA, Garber J, Kane M, Kolodner R. (1993) The human mutator gene homolog MSH2 and its association with hereditary nonpolyposis colon cancer. Cell. 75(5): 1027-1038.
Frazier ML, Xi L, Zong J, Viscofsky N, Rashid A, Wu EF, Lynch PM, Amos CI, Issa JP. (2003) Association of the CpG island methylator phenotype with family history of cancer in patients with colorectal cancer. Cancer Res. 63(16): 4805-4808.
Gao X, Wu N, Grignon D, Zacharek A, Liu H, Salkowski A, Li G, Sakr W, Sarkar F, Porter AT, et al. (1994) High frequency of mutator phenotype in human prostatic adenocarcinoma. Oncogene. 9(10): 2999-3003.
Grady WM, Myeroff LL, Swinler SE, Rajput A, Thiagalingam S, Lutterbaugh JD, Neumann A, Brattain MG, Chang J, Kim SJ, Kinzler KW, Vogelstein B, Willson JK, Markowitz S. (1999) Mutational inactivation of transforming growth factor beta receptor type II in microsatellite stable colon cancers. Cancer Res. 59(2): 320-324.
Gryfe R, Kim H, Hsieh ET, Aronson MD, Holowaty EJ, Bull SB, Redston M, Gallinger S. (2000) Tumor microsatellite instability and clinical outcome in young patients with colorectal cancer. N Engl J Med. 342(2): 69-77.
Halling KC, French AJ, McDonnell SK, Burgart LJ, Schaid DJ, Peterson BJ, Moon-Tasson L, Mahoney MR, Sargent DJ, O'Connell MJ, Witzig TE, Farr GH Jr, Goldberg RM, Thibodeau SN. (1999) Microsatellite instability and 8p allelic imbalance in stage B2 and C colorectal cancers. J Natl Cancer Inst. 91(15): 1295-1303.
Han HJ, Yanagisawa A, Kato Y, Park JG, Nakamura Y. (1993) Genetic instability in pancreatic cancer and poorly differentiated type of gastric cancer. Cancer Res. 53(21): 5087-5089.
Hawkins N, Norrie M, Cheong K, Mokany E, Ku SL, Meagher A, O'Connor T, Ward R. (2002) CpG island methylation in sporadic colorectal cancers and its relationship to microsatellite instability. Gastroenterology. 122(5): 1376-1387.
Ionov Y, Peinado MA, Malkhosyan S, Shibata D, Perucho M. (1993) Ubiquitous somatic mutations in simple repeated sequences reveal a new mechanism for colonic carcinogenesis. Nature. 363(6429): 558-561.
Kambara T, Simms LA, Whitehall VL, Spring KJ, Wynter CV, Walsh MD, Barker MA, Arnold S, McGivern A, Matsubara N, Tanaka N, Higuchi T, Young J, Jass JR, Leggett BA. (2004) BRAF mutation is associated with DNA methylation in serrated polyps and cancers of the colorectum. Gut. 53(8): 1137-1144.
Kumar R, Angelini S, Czene K, Sauroja I, Hahka-Kemppinen M, Pyrhönen S, Hemminki K (2003). BRAF mutations in metastatic melanoma: a possible association with clinical outcome. Clin Cancer Res. 9(9): 3362-3368.
Leach FS, Nicolaides NC, Papadopoulos N, Liu B, Jen J, Parsons R, Peltomäki P, Sistonen P, Aaltonen LA, Nyström-Lahti M, et al. (1993) Mutations of a mutS homolog in hereditary nonpolyposis colorectal cancer. Cell. 75(6): 1215-1225.
Liu B, Parsons R, Papadopoulos N, Nicolaides NC, Lynch HT, Watson P, Jass JR, Dunlop M, Wyllie A, Peltomäki P, de la Chapelle A, Hamilton SR, Vogelstein B, Kinzler KW. (1996) Analysis of mismatch repair genes in hereditary non-polyposis colorectal cancer patients. Nat Med. 2(2): 169-174.
Lothe RA, Peltomäki P, Meling GI, Aaltonen LA, Nyström-Lahti M, Pylkkänen L, Heimdal K, Andersen TI, Møller P, Rognum TO, et al. (1993) Genomic instability in colorectal cancer: relationship to clinicopathological variables and family history. Cancer Res. 53(24): 5849-5852.
Markowitz S, Wang J, Myeroff L, Parsons R, Sun L, Lutterbaugh J, Fan RS, Zborowska E, Kinzler KW, Vogelstein B, et al. (1995) Inactivation of the type II TGF-beta receptor in colon cancer cells with microsatellite instability. Science. 268(5215): 1336-1338.
Micka KA, Amiott EA, Hockenberry TL, Sprecher CJ, Lins AM, Rabbach DR, Taylor JA, Bacher JW, Glidewell DE, Gibson SD, Crouse CA, Schumm JW. (1999) TWGDAM validation of a nine-locus and a four-locus fluorescent STR multiplex system. J Forensic Sci. 44(6): 1243-1257.
Mironov NM, Aguelon MA, Potapova GI, Omori Y, Gorbunov OV, Klimenkov AA, Yamasaki H. (1994) Alterations of (CA)n DNA repeats and tumor suppressor genes in human gastric cancer. Cancer Res. 54(1): 41-44.
Nagasaka T, Sasamoto H, Notohara K, Cullings HM, Takeda M, Kimura K, Kambara T, MacPhee DG, Young J, Leggett BA, Jass JR, Tanaka N, Matsubara N. (2004) Colorectal cancer with mutation in BRAF, KRAS, and wild-type with respect to both oncogenes showing different patterns of DNA methylation. J Clin Oncol. 22(22): 4584-4594.
Nicolaides NC, Papadopoulos N, Liu B, Wei YF, Carter KC, Ruben SM, Rosen CA, Haseltine WA, Fleischmann RD, Fraser CM, et al. (1994) Mutations of two PMS homologues in hereditary nonpolyposis colon cancer. Nature. 371(6492): 75-80.
Park SJ, Rashid A, Lee JH, Kim SG, Hamilton SR, Wu TT. (2003) Frequent CpG island methylation in serrated adenomas of the colorectum. Am J Pathol. 162(3): 815-822.
Parsons R, Myeroff LL, Liu B, Willson JK, Markowitz SD, Kinzler KW, Vogelstein B. (1995) Microsatellite instability and mutations of the transforming growth factor beta type II receptor gene in colorectal cancer. Cancer Res. 55(23): 5548-5550.
Patel U, Grundfest-Broniatowski S, Gupta M, Banerjee S. (1994) Microsatellite instabilities at five chromosomes in primary breast tumors. Oncogene. 9(12): 3695-3700.
Paulson TG, Wright FA, Parker BA, Russack V, Wahl GM. (1996) Microsatellite instability correlates with reduced survival and poor disease prognosis in breast cancer. Cancer Res. 56(17): 4021-4026.
Peltomäki P, Lothe RA, Aaltonen LA, Pylkkänen L, Nyström-Lahti M, Seruca R, David L, Holm R, Ryberg D, Haugen A, et al. (1993) Microsatellite instability is associated with tumors that characterize the hereditary non-polyposis colorectal carcinoma syndrome. Cancer Res. 53(24): 5853-5855.
Planck M, Wenngren E, Borg A, Olsson H, Nilbert M. (2000) Somatic frameshift alterations in mononucleotide repeat-containing genes in different tumor types from an HNPCC family with germline MSH2 mutation. Genes Chromosomes Cancer. 29(1): 33-39.
Rajagopalan H, Bardelli A, Lengauer C, Kinzler KW, Vogelstein B, Velculescu VE. (2002) Tumorigenesis: RAF/RAS oncogenes and mismatch-repair status. Nature. 418(6901): 934.
Rhyu MG, Park WS, Meltzer SJ. (1994)Microsatellite instability occurs frequently in human gastric carcinoma. Oncogene. 9(1): 29-32.
Risinger JI, Berchuck A, Kohler MF, Watson P, Lynch HT, Boyd J. (1993) Genetic instability of microsatellites in endometrial carcinoma. Cancer Res. 53(21): 5100-5103.
Samowitz WS, Curtin K, Ma KN, Edwards S, Schaffer D, Leppert MF, Slattery ML. (2002) Prognostic significance of p53 mutations in colon cancer at the population level. Int J Cancer. 99(4): 597-602.
Samowitz WS, Curtin K, Schaffer D, Robertson M, Leppert M, Slattery ML. (2000) Relationship of Ki-ras mutations in colon cancers to tumor location, stage, and survival: a population-based study. Cancer Epidemiol Biomarkers Prev. 9(11): 1193-1197.
Samowitz WS, Curtin K, Ma KN, Schaffer D, Coleman LW, Leppert M, Slattery ML. (2001) Microsatellite instability in sporadic colon cancer is associated with an improved prognosis at the population level. Cancer Epidemiol Biomarkers Prev. 10(9): 917-923.
Samowitz WS, Holden JA, Curtin K, Edwards SL, Walker AR, Lin HA, Robertson MA, Nichols MF, Gruenthal KM, Lynch BJ, Leppert MF, Slattery ML. (2001) Inverse relationship between microsatellite instability and K-ras and p53 gene alterations in colon cancer. Am J Pathol. 158(4): 1517-1524.
Samowitz WS, Sweeney C, Herrick J, Albertsen H, Levin TR, Murtaugh MA, Wolff RK, Slattery ML. (2005) Poor Survival Associated with the BRAF V600E Mutation in Microsatellite-Stable Colon Cancers. Cancer Res. 65(14): 6063-6069.
Sia EA, Kokoska RJ, Dominska M, Greenwell P, Petes TD. (1997) Microsatellite instability in yeast: dependence on repeat unit size and DNA mismatch repair genes. Mol Cell Biol. 17(5): 2851-2858.

(56) References Cited

OTHER PUBLICATIONS

Slattery ML, Potter J, Caan B, Edwards S, Coates A, Ma KN, Berry TD. (1997) Energy balance and colon cancer—beyond physical activity. Cancer Res. 57(1): 75-80.

Thibodeau SN, Bren G, Schaid D. (1993) Microsatellite instability in cancer of the proximal colon. Thibodeau SN, Bren G, Schaid D. Science. 260(5109): 816-819.

Toyota M, Ahuja N, Ohe-Toyota M, Herman JG, Baylin SB, Issa JP. (1999) CpG island methylator phenotype in colorectal cancer. Proc Natl Acad Sci USA. 96(15): 8681-8686.

Toyota M, Ohe-Toyota M, Ahuja N, Issa JP. (2000) Distinct genetic profiles in colorectal tumors with or without the CpG island methylator phenotype. Proc Natl Acad Sci USA. 97(2): 710-715.

van Rijnsoever M, Grieu F, Elsaleh H, Joseph D, Iacopetta B. (2002) Characterisation of colorectal cancers showing hypermethylation at multiple CpG islands. Gut. 51(6): 797-802.

Wan PT, Garnett MJ, Roe SM, Lee S, Niculescu-Duvaz D, Good VM, Jones CM, Marshall CJ, Springer CJ, Barford D, Marais R. (2004) Mechanism of activation of the RAF-ERK signaling pathway by oncogenic mutations of B-RAF. Cell. 116(6): 855-867.

Wang L, Cunningham JM, Winters JL, Guenther JC, French AJ, Boardman LA, Burgart LJ, McDonnell SK, Schaid DJ, Thibodeau SN. (2003) BRAF mutations in colon cancer are not likely attributable to defective DNA mismatch repair. Cancer Res. 63(17): 5209-5012.

Ward RL, Williams R, Law M, Hawkins NJ. (2004) The CpG island methylator phenotype is not associated with a personal or family history of cancer. Cancer Res. 64(20): 7618-7621.

Wilhelm SM, Carter C, Tang L, Wilkie D, McNabola A, Rong H, Chen C, Zhang X, Vincent P, McHugh M, Cao Y, Shujath J, Gawlak S, Eveleigh D, Rowley B, Liu L, Adnane L, Lynch M, Auclair D, Taylor I, Gedrich R, Voznesensky A, Riedl B, Post LE, Bollag G, Trail PA. (2004) BAY 43-9006 exhibits broad spectrum oral antitumor activity and targets the RAF/MEK/ERK pathway and receptor tyrosine kinases involved in tumor progression and angiogenesis. Cancer Res. 64(19): 7099-7109.

Yamamoto H, Sawai H, Weber TK, Rodriguez-Bigas MA, Perucho M. (1998) Somatic frameshift mutations in DNA mismatch repair and proapoptosis genes in hereditary nonpolyposis colorectal cancer. Cancer Res. 58(5): 997-1003.

Young J, Barker MA, Simms LA, Walsh MD, Biden KG, Buchanan D, Buttenshaw R, Whitehall VL, Arnold S, Jackson L, Kambara T, Spring KJ, Jenkins MA, Walker GJ, Hopper JL, Leggett BA, Jass JR. (2005) Evidence for BRAF mutation and variable levels of microsatellite instability in a syndrome of familial colorectal cancer. Clin Gastroenterol Hepatol. 3(3): 254-263.

Yuen ST, Davies H, Chan TL, Ho JW, Bignell GR, Cox C, Stephens P, Edkins S, Tsui WW, Chan AS, Futreal PA, Stratton MR, Wooster R, Leung SY. (2002) Similarity of the phenotypic patterns associated with BRAF and KRAS mutations in colorectal neoplasia. Cancer Res. 62(22): 6451-6455.

International Search Report, dated Mar. 5, 2007 for PCT Application No. PCT/US06/027130.

Written Opinion, dated Mar. 5, 2007 for PCT Application No. PCT/US06/027130.

International Preliminary Report on Patentability, dated Jul. 8, 2008 for PCT Application No. PCT/US06/027130.

\* cited by examiner

|  | Status at end of follow-up | | | | |
| --- | --- | --- | --- | --- | --- |
|  | Dead | | Alive | | 5-yr survival |
|  | N | (%) | N | (%) | (% alive) |
| Age at time of diagnosis | | | | | |
| <55 | 56 | 43.1 | 74 | 56.9 | 57.5 |
| 55-64 | 107 | 43.7 | 138 | 56.3 | 66.4 |
| 65-70 | 110 | 45.8 | 130 | 54.2 | 70.8 |
| 71-79 | 200 | 55.4 | 161 | 44.6 | 62.8 |
| p | | | | | 0.08 |
| Gender | | | | | |
| Male | 254 | 48.8 | 266 | 51.2 | 68.1 |
| Female | 219 | 48.0 | 237 | 52.0 | 61.7 |
| p | | | | | 0.05 |
| Tumor Site | | | | | |
| Proximal | 241 | 50.8 | 233 | 49.2 | 62.0 |
| Distal | 215 | 45.6 | 257 | 54.4 | 68.9 |
| p | | | | | 0.04 |
| AJCC Stage | | | | | |
| 1 | 61 | 26.2 | 172 | 73.8 | 94.3 |
| 2 | 97 | 35.7 | 175 | 64.3 | 83.9 |
| 3 | 146 | 52.1 | 134 | 47.9 | 60.3 |
| 4 | 164 | 92.1 | 14 | 7.9 | 9.3 |
| p | | | | | <.01 |
| Differentiation | | | | | |
| Well | 28 | 32.6 | 58 | 67.4 | 88.7 |
| Moderate | 313 | 47.8 | 342 | 52.2 | 66.7 |
| Poor | 92 | 56.8 | 70 | 43.2 | 50.0 |
| p | | | | | <.01 |
| MSI | | | | | |
| Stable | 425 | 49.4 | 436 | 50.6 | 62.9 |
| Unstable | 27 | 31.0 | 60 | 69.0 | 89.0 |
| p | | | | | <.01 |
| CIMP 1 | | | | | |
| Low | 303 | 48.3 | 324 | 51.7 | 66.3 |
| High | 133 | 49.4 | 136 | 50.6 | 61.9 |
| p | | | | | 0.24 |
| BRAF | | | | | |
| Wt | 398 | 46.6 | 456 | 53.4 | 66.4 |
| Mut | 54 | 60.7 | 35 | 39.3 | 54.5 |
| p | | | | | 0.04 | p is a Chi-squared statistic for differences in 5-yr survival.

FIG. 4

METHODS AND COMPOSITIONS RELATED TO A BRAF MUTATION AND MICROSATELLITE STABILITY

CROSS REFERENCE TO RELATED APPLICATIONS

This application claims the benefit of priority under 35 U.S.C. § 371 of International Application No. PCT/US2006/027130, filed on Jul. 13, 2006, which claims priority to U.S. Provisional Application No. 60/699,011, filed on Jul. 13, 2005. The content of these earlier filed applications is hereby incorporated by reference herein in their entirety.

STATEMENT REGARDING FEDERALLY FUNDED RESEARCH

This invention was made with government support under Grant RO1 CA 61757 awarded by National Institutes of Health. The government has certain rights in the invention.

I. BRIEF DESCRIPTION OF THE DRAWINGS

The accompanying drawings, which are incorporated in and constitute a part of this specification, illustrate several embodiments and together with the description illustrate the disclosed compositions and methods.

FIG. 4 shows status at the end of follow up for patients described in Example 1.

II. DETAILED DESCRIPTION

Figure 1:
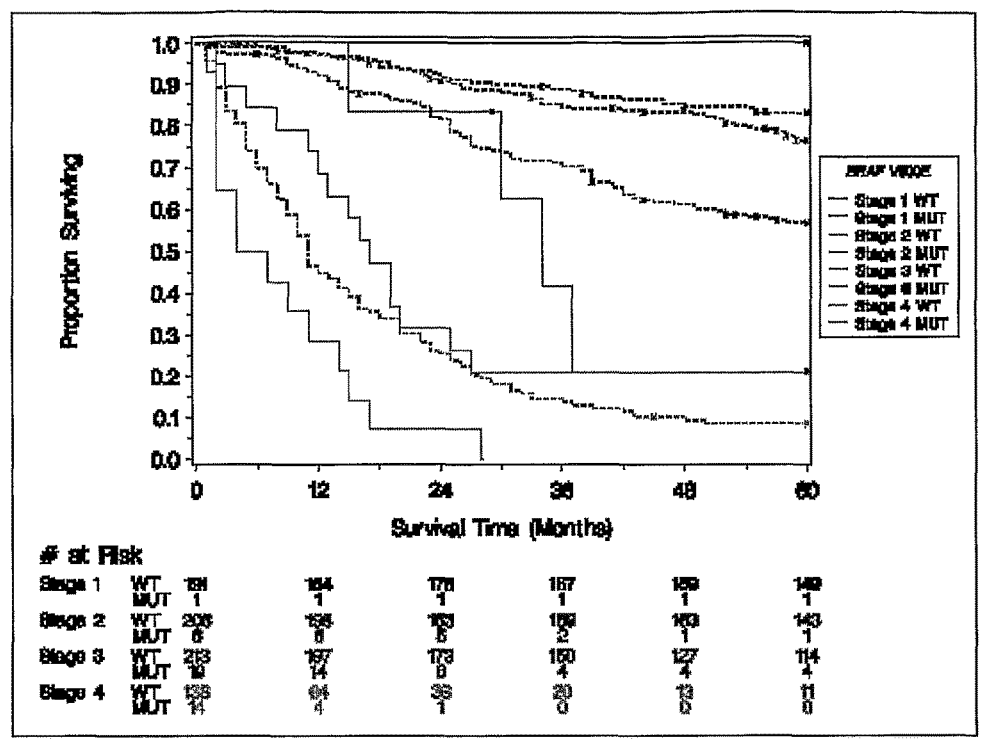
FIG. 1 shows Kaplan-Meier survival estimates comparing the overall survival of V600E BRAF mutation versus BRAF WT for microsatellite-stable colon cancers. Although relatively few numbers of tumors are present at each stage, tumors with the V600E BRAF mutations had a significantly higher risk of death than BRAF WT tumors for stages 2 to 4 (P<0.01, log-rank test).

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

By "sample" is meant any body fluid (e.g., but not limited to, blood, serum, urine, cerebrospinal fluid, semen, sputum, saliva, tears, joint fluids, body cavity fluids (e.g., peritoneal fluid), or washings), tissue, or organ obtained from a subject; a cell (either within a subject, taken directly from a subject, or a cell maintained in culture or from a cultured cell line); a lysate (or lysate fraction) or extract derived from a cell; or a molecule derived from a cell or cellular material.

By "modulate" is meant to alter, by increase or decrease.

By "increase in gene expression level," "expressed at an increased level," "increased expression," and similar phrases is meant a rise in the relative amount of mRNA or protein, e.g., on account of an increase in transcription, translation, mRNA stability, or protein stability, such that the overall amount of a product of the gene, i.e., an mRNA or polypeptide, is augmented. Preferably the increase is by at least about 3-fold, more preferably, by at least about: 4-fold, 5-fold, 7-fold, 10-fold, 15-fold, 20-fold, 30-fold, 40-fold, 50-fold, 70-fold, or more.

By "decrease in gene expression level" is meant a reduction in the relative amount of mRNA or protein transcription, translation, mRNA stability, or protein stability, such that the overall amount of a product of the gene, i.e., an mRNA or polypeptide, is reduced. Preferably the decrease is by at least about 20%-25%, more preferably by at least about 26%-50%, still more preferably by at least about 51%-75%, even more preferably by at least about 76%-95%, and most preferably, by about 96%-100%.

By "modulating production or activity of a polypeptide" is meant to increase or decrease gene expression level, as described above, or to stimulate or inhibit the ability of a tumor polypeptide to perform its intrinsic biological function (examples of such functions include, but are not limited to, enzymatic activity, e.g., kinase activity or GTPase activity; cell-signaling activity, e.g., activation of a growth factor receptor; or cell adhesion activity. The modulation may be an increase in the amount of the polypeptide produced or an increase in the activity of the polypeptide, of at least about: 2-fold, 4-fold, 6-fold, or 10-fold, or the modulation may be a decrease in the amount of the polypeptide produced or a decrease in the activity of the polypeptide, of at least about: 20%-25%, 26%-50%, 51%-75%, 76%-95%, or 96%-100%. These increases and/or decreases are compared with the amount of production and/or activity in a normal cell, sample, or subject.

By "effective amount" of a compound as provided herein is meant a nontoxic but sufficient amount of the compound to provide the desired effect, e.g., modulation of tumor activity. As will be pointed out below, the exact amount required will vary from subject to subject, depending on the species, age, and general condition of the subject, the severity and type of disease that is being treated, the particular compound used, its mode of administration, and the like. Thus, it is not possible to specify an exact "effective amount." However, an appropriate "effective amount" may be determined by one of ordinary skill in the art using only routine experimentation.

By "having an increased risk" is meant a subject that is identified as having a higher than normal chance of developing cancer, compared to the general population. In addition, a subject who has had, or who currently has, cancer is a subject who has an increased risk for developing cancer, as such a subject may continue to develop cancer. Subjects who currently have, or who have had, a tumor also have an increased risk for tumor metastases.

By "treat" is meant to administer a compound or molecule of the invention to a subject in order to: eliminate cancer or reduce the size of a tumor or the number of tumors in a subject; arrest or slow the growth of a tumor in a subject; inhibit or slow the development of a new tumor or tumor metastasis in a subject; or decrease the frequency or severity of symptoms and/or recurrences in a subject who currently has or who previously has had cancer.

By "prevent" is meant to minimize the chance that a subject will develop cancer or to delay the development of cancer. For example, a person at increased risk for cancer, as described above, would be a candidate for therapy to prevent cancer.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. GENERAL

Disclosed herein are methods for diagnosis and prognosis evaluation for cancer, as well as methods for screening for compositions which modulate cancer and compositions which bind to modulators of cancer. Also disclosed are methods of treating cancer. In one aspect, the expression of genes, and the assaying of proteins (including microsatellites) are determined in different subjects for which either diagnosis or prognosis information is desired, to provide cancer profiles. Within the cancer tissue, different prognosis states (good or poor long term survival prospects, for example) may be determined. By comparing profiles of cancer tissue in different states, information regarding which genes are important (including both up- and down-regulation of genes) in each of these states is obtained. The identification of sequences that are differentially expressed in cancer tissue, as well as differential expression resulting in different prognostic outcomes, allows the use of this information in a number of ways. For example, the evaluation of a particular treatment regime may be evaluated: does a chemotherapeutic drug act to improve the long-term prognosis in a particular patient. Similarly, diagnosis may be done or confirmed by comparing subjects with the known profiles. Furthermore, these cancer profiles allow screening of drug candidates with an eye to mimicking or altering a particular cancer profile; for example, screening can be done for drugs that suppress the cancer profile or convert a poor prognosis profile to a better prognosis profile. This may be done by making biochips comprising sets of the important genes of interest, which can then be used in these screens. These methods can also be done on the protein basis; that is, protein levels can be evaluated for diagnostic and prognostic purposes or to screen candidate agents. In addition, the cancer can be assayed for microsatellite stability, and the results used with the methods disclosed herein.

BRAF is a part of the Ras/Raf/MEK/MAP signal transduction pathway, and oncogenic mutations in BRAF, including the V600E mutation, have been reported in various types of cancer, including colon cancer (Davies et al. Nature 417:949-54 (2002); Rajagopalan et al. Nature 418:934 (2002)). This mutation has been observed in over half of all microsatellite-unstable carcinomas and in a much smaller subset of stable colon tumors (Rajagopalan et al. (2002), Wang et al. Cancer Res 63: 5209-12 (2003)). In both stable and unstable cancers, >90% of tumors with BRAF mutations have widespread methylation of CpG islands or what is known as the CpG island methylator phenotype (CIMP). An improved survival is associated with microsatellite instability (MSI) in sporadic colon cancers (Samowitz et al. Cancer Epidemiol Biomarkers Prev 10:917-23 (2001); Halling et al. J Natl Cancer Inst 91:1295-303 (1999)), and because sporadic unstable tumors commonly show both CIMP and BRAF mutations (Rajagopalan et al. (2002)., Wang et al. (2003), Kambara et al. Gut 53:1137-44 (2004), Nagasaka et al. J Clin Oncol 22:4584-94 (2004)), one would expect that these features would also show a relationship to improved survival in unstable tumors.

The BRAF V600E mutation has been associated with microsatellite instability and the CpG island methylator phenotype (CIMP) in cancer, as disclosed above. A large population-based sample of individuals with colon cancer was studied in order to determine its relationship to survival and other clinicopathologic variables (Example 1). The V600E BRAF mutation was seen in 5% (40 of 803) of microsatellite-stable tumors and 51.8% (43 of 83) of microsatellite-unstable tumors. In microsatellite-stable tumors, this mutation was related to poor survival, CIMP high, advanced American Joint Committee on Cancer (AJCC) stage, and family history of colorectal cancer. The poor survival was observed in a univariate analysis of 5-year survival (16.7% versus 60.0%; P<0.01); in an analysis adjusted for age, stage, and tumor site; in stage-specific, age-adjusted analyses for AJCC stages 2 to 4 (HRR, 4.88, 3.60, and 2.04, respectively); and in Kaplan-Meier survival estimates for AJCC stages 2 to 4 (P<0.01 for all three stages). Microsatellite-unstable tumors were associated with an excellent 5-year survival whether the V600E mutation was present or absent (76.2% and 75.0%, respectively). It was concluded that the BRAF V600E mutation in microsatellite-stable colon cancer is associated with a significantly poorer survival in stages 2 to 4 colon cancer but has no effect on the excellent prognosis of microsatellite-unstable tumors. (Cancer Res 65(14):1-8 (2005)).

The mitogen-activated protein kinase (MAPK) pathway mediates cellular responses to growth signals and activation of this pathway has been shown to be critical in tumor formation, such as in melanomas. Activating BRAF mutations have been found with high frequency in malignant melanomas, including primary tumors and cell lines. Suppression of activating BRAF mutations in cultured human melanoma cells inhibits the MAPK cascade causing growth arrest and promoting apoptosis, showing a critical role of activating BRAF mutations in malignant transformation. Therefore, there is clinical significance of BRAF mutations in metastatic melanoma (Chang et al., Journal of Translational Medicine 2004, 2:46).

Microsatellite Stability

A microsatellite locus is a region of genomic DNA with simple tandem repeats that are repetitive units of one to five base pairs in length. Hundreds of thousands of such microsatellite loci are dispersed throughout the human genome. Microsatellite loci are classified based on the length of the smallest repetitive unit. For example, loci with repetitive units of 1 to 5 base pairs in length are termed "mononucleotide", "di-nucleotide", "tri-nucleotide", "tetra-nucleotide", and "penta-nucleotide" repeat loci, respectively.

Detection of MSI is known in the art, and one of skill in the art can determine which method to use with those methods disclosed herein. Each microsatellite locus of normal genomic DNA for most diploid species, such as genomic DNA from mammalian species, consists of two alleles at each locus. The two alleles can be the same or different from one another in length and can vary from one individual to the next. Microsatellite alleles are normally maintained at constant length in a given individual and its descendants; but, instability in the length of microsatellites has been observed in some tumor types (Aaltonen et al., 1993, Science 260:812-815; Thibodeau et al., 1993 Science 260:816-819; Peltomaki et al., 1993 Cancer Research 53:5853-5855; Ionov et al., 1993 Nature 363:558-561). This form of genomic instability in tumors, termed microsatellite instability (also referred to herein as, "MSI"), is a molecular hallmark of the inherited cancer syndrome Hereditary Nonopolyposis Colorectal Cancer (hereinafter, "HNPCC"). The cause of MSI in HNPCC is thought to be a dysfunctional DNA mismatch repair system that fails to reverse errors that occur during DNA replication (Fishel et al., 1993 Cell 75:1027-38; Leach et al., 1993 Cell 75:215-25; Bronner et al., 1994 Nature 368:258-61; Nicolaides et al., 1994 Nature 371:75-80; Miyaki et al., 1997 Nat Genetics 17:271-2). Insertion or deletion of one or more repetitive units during DNA replication persists without mismatch repair and can be detected as length polymorphisms by comparison of allele sizes found in microsatellite loci amplified from normal and tumor DNA samples (Thibodeau et al, 1993, supra).

MSI has been found in over 90% of HNPCC and in 10-20% of sporadic colorectal tumors (Liu et al., 1996 Nature Med 2:169-174; Thibodeau et al., 1993, supra; Ionov et al., 1993 Nature 363:558-561; Aaltonen et al., 1993 Science 260: 812-816; Lothe et al., 1993 Cancer Res. 53: 5849-5852). However, MSI is not limited to colorectal tumors. MSI has also been detected in pancreatic cancer (Han et al., 1993 Cancer Res 53:5087-5089) gastric cancer (Id.; Peltomaki et al., 1993 Cancer Res 53:5853-5855; Mironov et al., 1994 Cancer Res 54:41-44; Rhyu et al., 1994 Oncogene 9:29-32; Chong et al., 1994 Cancer Res 54:4595-4597), prostate cancer (Gao et al., 1994 Oncogene 9:2999-3003), endometrial cancer (Risinger et al., 1993 Cancer Res 53:5100-5103; Peltomaki et al., 1993 Cancer Res 53:5853-5855), and breast cancer (Patel et al., 1994 Oncogene 9:3695-3700).

Repetitive DNA is particularly sensitive to errors in replication and therefore dysfunctional mismatch repair systems result in widespread alterations in microsatellite regions. A study of yeast cells without functional mismatch repair systems showed a 2800, 284, 52, and 19 fold increase in mutation rates in mono-, di-, tri-, tetra-, and pentanucleotide repeats, respectively (Sia et al., 1997 Molecular and Cellular Biology 17:2851-2858). Mutations in mismatch repair genes are not thought to play a direct role in tumorigenesis, but rather act by allowing DNA replication errors to persist. Mismatch repair deficient cells have high mutation rates and if these mutations occur in genes involved in tumorigenesis the result can lead to the development of cancer. MSI positive tumors have been found to carry somatic frameshift mutations in mono-nucleotide repeats in the coding region of several genes involved in growth control, apoptosis, and DNA repair (e.g., TGFBRII, BAX, IGFIIR, TCF4, MSH3, MSH6) (Planck et al., 2000 Genes, Chromosomes & Cancer 29:33-39; Yamamoto et al., 1998 Cancer Research 58:997-1003; Grady et al., 1999 Cancer Research 59:320-324; Markowitz et al., 1995 Science 268: 1336-1338; Parsons et al., 1995 Cancer Research 55:5548-5550). The most commonly altered locus is TGFBRII, in which over 90% of MSI-H colon tumors have been found to contain a mutation in the 10 base polyadenine repeat present in the gene (Markowitz et al., 1995 Science 268:1336-1338).

MSI occurs in almost all HNPCC tumors regardless of which mismatch repair gene is involved. MSI has also been shown to occur early in tumorigenesis. These two factors contribute to making MSI analysis an excellent diagnostic test for the detection of HNPCC. In addition, MSI analysis can serve as a useful pre-screening test to identify potential HNPCC patients for further genetic testing. MSI analysis of sporadic colorectal carcinomas is also desirable, since the occurrence of MSI correlates with a better prognosis (Bertario et al., 1999 International J Cancer 80:83-7).

Clinical diagnostic assays used for determining treatment and prognosis of disease require that the tests be highly accurate (low false negatives) and specific (low false positive rate). Many informative microsatellite loci have been identified and recommended for MSI testing (Boland et al. 1998, supra). Multiple markers can be used to increase the power of detection, and can be used in conjunction with multiplexing. Multiplexing allows simultaneous amplification and analysis of a set of loci in a single tube and can often reduce the total amount of DNA required for complete analysis. To increase the specificity of an MSI assay for any given type of cancer, it has been recommended that the panel of five highly informative microsatellite loci identified at the National Institute Workshop be modified to substitute or add other loci of equal utility (Boland et al. 1998, supra, at p.

5250). Increased information yielded from amplifying and analyzing greater numbers of loci results in increased confidence and accuracy in interpreting test results.

One method of multiplex analysis of microsatellite loci contemplates selecting an appropriate set of loci, primers, and amplification protocols to generate amplified alleles from multiple co-amplified loci which preferably do not overlap in size or, more preferably, which are labeled in a way which enables one to differentiate between the alleles from different loci which overlap in size. Combinations of loci may be rejected for either of the above two reasons, or because, in combination, one or more of the loci do not produce adequate product yield, or fragments which do not represent authentic alleles are produced in this reaction.

The following factors are preferably taken into consideration in deciding upon which loci to include in a multiplex of the present invention. To effectively design the microsatellite multiplex, size ranges for alleles at each locus are determined. This information is used to facilitate separation of alleles between all the different loci, since any overlap could result in an allele from one locus being inappropriately identified as instability at another locus.

The amount of stutter exhibited by non-mononucleotide repeat loci is also preferably taken into consideration; as the amount of stutter exhibited by a locus can be a major factor in the ease and accuracy of interpretation of data. It is preferable to conduct a population study to determine the level of stutter present for each non-mono-nucleotide repeat locus. As noted above, tetra-nucleotide repeat markers display considerably less stutter that shorter repeat types like di-nucleotides and therefore can be accurately scored in MSI assays (Bacher & Schumm, 1998 Profiles in DNA 2(2):3-6). Note that even within a class of microsatellite loci, such as tetra- and penta-nucleotide repeat loci, known to exhibit low stutter, the percent stutter can vary considerably within the repeat type (Micka et al., 1999, supra).

Although at least one mono-nucleotide and at least two tetra-nucleotide repeat loci are included in the multiplex of MSI loci co-amplified according to the method or using the kit of the present invention, additional mono-nucleotide and/or tetra-nucleotide repeat loci can be included in the multiplex. It is also contemplated that multisatellite loci other than mono- or tetra-nucleotide repeat loci meeting the same or similar criteria to the criteria described above would be included in the multiplex.

C. COMPOSITIONS

Disclosed herein is the BRAF polypeptide (GenBank Accession No. P15056), and mutations occurring therein. Several BRAF mutations have been identified, including V600E. Another three mutations occurred in codon 594 (D594N, D594G, and D594G) and were present in microsatellite-stable, CIMP low tumors. All of these individuals survived at least 5 years (although all were relatively low-stage tumors). The fourth mutation (G606R) occurred in a microsatellite-stable, CIMP high tumor and was associated with death due to colon cancer after 19 months.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular sequence is disclosed and discussed and a number of modifications that can be made to a number of molecules including the sequence are discussed, specifically contemplated is each and every combination and permutation of the sequence, and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154: 367, 1987 which is herein incorporated by reference for material at least related to hybridization of nucleic acids). A preferable stringent hybridization condition for a DNA: DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

3. Nucleic Acids

There are a variety of molecules disclosed herein that are nucleic acid based, including for example the nucleic acids that encode, for example BRAF, or any of the nucleic acids disclosed herein for making BRAF mutations, or fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell that the expressed mRNA will typically be made up of A, C, G, and U. Likewise, it is understood that if, for example, an antisense molecule is introduced into a cell or cell environment through for example exogenous delivery, it is advantagous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to the protein molecules involved in the signaling pathways disclosed herein, for example BRAF, or any of the nucleic acids disclosed herein for making BRAF, all of which are encoded by nucleic acids or are nucleic acids. The sequences for the human analogs of these genes, as well as other analogs, and alleles of these genes, and splice variants and other types of variants, are available in a variety of protein and gene databases, including Genbank. Those sequences available at the time of filing this application at Genbank are herein incorporated by reference in their entireties as well as for individual subsequences contained therein. Genbank can be accessed at http://www.ncbi.nih.gov/entre71query.fcgi. Those of skill in the art understand how to resolve sequence discrepancies and differences and to adjust the compositions and methods relating to a particular sequence to other related sequences. Primers and/or probes can be designed for any given sequence given the information disclosed herein and known in the art.

c) Primers and Probes

Disclosed are compositions including primers and probes, which are capable of interacting with the disclosed nucleic acids, such as the BRAF polypeptide and microsatellite DNA as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the BRAF gene typically will be used to produce an amplified DNA product that contains a region of the BRAF gene or the complete gene, including mutations thereof. In general, typically the size of the product will be such that the size can be accurately determined to within 3, or 2 or 1 nucleotides.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

4. Peptides a) Protein Variants

As discussed herein there are numerous variants of the BRAF protein that are known and herein contemplated. In addition, to the known functional BRAF strain variants there are derivatives of the BRAF proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

65.

TABLE 1

Amino Acid Abbreviations

| Amino Acid | Abbreviations |
|---|---|
| alanine | Ala, A |
| arginine | Arg, R |
| asparagine | Asn, N |
| aspartic acid | Asp, D |
| cysteine | Cys, C |
| glutamic acid | Glu, E |
| glutamine | Gln, Q |
| glycine | Gly, G |
| histidine | His, H |
| isolelucine | Ile, I |
| leucine | Leu, L |
| lysine | Lys, K |
| phenylalanine | Phe, F |
| proline | Pro, P |
| methionine | Met, M |
| serine | Ser, S |
| threonine | Thr, T |
| tyrosine | Tyr, Y |
| tryptophan | Trp, W |
| valine | Val, V |

TABLE 2

Amino Acid Substitutions
Original Residue Exemplary Conservative
Substitutions, others are known in the art.

Ala, ser
Arg, lys, gln
Asn, gln; his
Asp, glu
Cys, ser
Gln, asn, lys
Glu, asp
Gly, pro
His, asn; gln
Ile, leu; val
Leu, ile; val
Lys, arg; gln;
Met, Leu; ile
Phe, met; leu; tyr
Ser, thr TABLE 2-continued Amino Acid Substitutions
Original Residue Exemplary Conservative
Substitutions, others are known in the art.

Thr, ser
Trp, tyr
Tyr, trp; phe
Val, ile; leu

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is understood that while no amino acid sequence indicates what particular DNA sequence encodes that protein within an organism, where particular variants of a disclosed protein are disclosed herein, the known nucleic acid sequence that encodes that protein in the particular nucleic acid from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, —CH(OH) $CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CH $H_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH) $CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

5. Antibodies (1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with BRAF or a microsatellite such that the molecule is inhibited.

Examples of molecules that inhibit BRAF include, but are not limited to, those developed by Ambit technologies (http://www.ambitbio.com/products/braf.htm); those developed by ArQule, such as ARQ 501, ARQ 197, ARQ 171, ARQ-450RP, ARQ-350RP, ARQ-250RP, ARQ-700RP ARQ-300RP, ARQ-800RP, ARQ-150RP, and ARQ-850RP (http://www.arqule.com/wt/arc/research); those being refined by Wellcome Trust and Astex Technology Ltd; PLX4032, Plexxickon's oncogenic BRAF inhibitor (http://www.plexxikon.com/release-040306.shtml); Nexavar (sorafenib), which is produced by Bayer/Onyx and was approved in December 2005 by the FDA.

Antibodies that bind the disclosed regions of BRAF, for example, are also disclosed. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA*, 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boemer et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,* 90:2551-255 (1993); Jakobovits et al., *Nature,* 362:255-258 (1993); Bruggermann et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, FV framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature,* 321:522-525 (1986), Reichmann et al., *Nature,* 332:323-327 (1988), and Presta, *Curr. Opin. Struct. Biol.,* 2:593-596 (1992)).

Methods for humanizing non-human antibodies are well known in the art. For example, humanized antibodies can be generated according to the methods of Winter and coworkers (Jones et al., *Nature,* 321:522-525 (1986), Riechmann et al., *Nature,* 332:323-327 (1988), Verhoeyen et al., *Science,* 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

(4) Administration of Antibodies

Administration of the antibodies can be done as disclosed herein. Nucleic acid approaches for antibody delivery also exist. The broadly neutralizing anti BRAF antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

6. Pharmaceutical Carriers/Delivery of Pharmaceutical Products

The compositions disclosed herein can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

Other molecules that interact with BRAF to inhibit cancer interactions which do not have a specific pharmaceutical function, but which may be used for tracking changes within cellular chromosomes or for the delivery of diagnostic tools for example can be delivered in ways similar to those described for the pharmaceutical products.

The disclosed compositions and methods can also be used for example as tools to isolate and test new drug candidates for a variety of cancers and related diseases.

7. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

8. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein.

9. Compositions Identified by Screening with Disclosed Compositions/Combinatorial Chemistry a) Combinatorial Chemistry The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed in BRAF or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, compositions to be used in treatment, are also disclosed. Thus, the products produced using the combinatorial or screening approaches that involve the disclosed compositions are also considered herein disclosed.

It is understood that the disclosed methods for identifying molecules that inhibit the BRAF mutation, for example, can be performed using high through put means. For example, putative inhibitors can be identified using Fluorescence Resonance Energy Transfer (FRET) to quickly identify interactions. The underlying theory of the techniques is that when two molecules are close in space, i.e., interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately 10" individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci, USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23)12997-302 (1997)).

Another preferred method for combinatorial methods designed to isolate peptides is described in Cohen et al. (Cohen B. A., et al., Proc. Natl. Acad. Sci. USA 95(24): 14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example an extracellular portion of BRAF is attached to a DNA binding domain of a transcriptional activation protein, such as Gal 4. By performing the Two-hybrid technique on this type of system, molecules that bind the extracellular portion of BRAF can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2, 3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

Screening molecules similar to BRAF for inhibition of a BRAF mutation is a method of isolating desired compounds. As used herein combinatorial methods and libraries included traditional screening methods and libraries as well as methods and libraries used in interative processes.

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as BRAF and associated mutations, are also disclosed. Thus, the products produced using the molecular modeling approaches that involve the disclosed compositions, such as, BRAF and associated mutations, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *OSAR: Quantitative Structure—Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

10. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for assessing a subject's risk for acquiring colon cancer.

11. Compositions with Similar Functions

It is understood that the compositions disclosed herein have certain functions, such as in detection or inhibition. Disclosed herein are certain structural requirements for performing the disclosed functions, and it is understood that there are a variety of structures which can perform the same function which are related to the disclosed structures, and that these structures will ultimately achieve the same result, for example stimulation or inhibition.

D. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.,* 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

E. METHODS OF USING THE COMPOSITIONS

1. Methods of Using the Compositions as Research Tools

Disclosed herein are methods of prognosing survival rates in a subject with cancer comprising: a) testing a sample from the subject for microsatellite stability; b) testing a sample from the subject for a BRAF mutation; c) analyzing results from steps a) and b), wherein the results are indicative of survival rates.

Cancer survival rates or survival statistics are used to show the percentage of people who survive a certain type of cancer for a specific amount of time. Cancer statistics often use a five-year survival rate. An overall survival rate includes people of all ages and health conditions diagnosed with that type of cancer. Because a BRAF mutation and microsatellite stability are associated with a poor prognosis, the chance of survival for an individual at given intervals can be calculated based on this information. The survival rate, for example, can be used to show disease-free survival rate, which is the number of people with a given type of cancer who achieve remission. An alternative is a progression-free survival rate. This is the number of people who still have cancer, but their disease isn't progressing.

Also disclosed is a method of classifying the severity of cancer in a subject, comprising a) testing a sample from the subject for microsatellite stability; b) testing a sample from the subject for a BRAF mutation; c) analyzing results from steps a) and b), wherein the results are indicative of the severity of the cancer.

Similarly, disclosed are methods of determining the prognosis of a subject with cancer, comprising a) testing a sample from the subject for microsatellite stability; b) testing a sample from the subject for a BRAF mutation; c) analyzing results from steps a) and b), wherein the results determine the prognosis of the subject with cancer.

Prognosis can occur in several fashions. One is correlated with the stage of the disease. For example, colon cancer can be shown in various stages, and the prognosis based upon this. If the patient's colon cancer does not come back (recur) within 5 years, it is considered cured. This is because colon cancer rarely comes back after 5 years. Traditionally, stage I, II, and III cancers are considered potentially curable. Stage I has a 90% 5-year survival. Stage II has a 75-85% 5-year survival, and Stage III a 40-60% 5-year survival. These numbers take into account that for stage III patients (and in some studies, stage II patients) chemotherapy improves the chance of 5-year survival. Patients with stage IV disease rarely live beyond five years and the median survival (meaning half the patients live longer, and half shorter) with treatment is between 1 and 2 years.

As disclosed herein, a subject who has been found to have a BRAF mutation, as well a microsatellite stable cancer, will have a poorer prognosis than those with other combinations. Traditionally, for example, those diagnosed with stage II colon cancer are often not treated. However, in the scenario described herein, where the subject has a BRAF mutation and microsatellite-stable cancer, the subject can be treated more aggressively, thereby giving the subject a better prognosis, and therefore a higher chance of survival Also disclosed are methods of treating a subject with cancer, comprising a) testing a sample from the subject for microsatellite stability; b) testing a sample from the subject for a BRAF mutation; c) analyzing results from steps a) and b), and d) treating the subject according to the outcome.

For example, the subject can be treated with a BRAF mutation inhibitor. One such example is BAY 43-9006. The RAS/RAF signaling pathway is an important mediator of tumor cell proliferation and angiogenesis. The novel bi-aryl urea BAY 43-9006 is a potent inhibitor of Raf-1, a member of the RAF/MEK/ERK signaling pathway. Additional characterization showed that BAY 43-9006 suppresses both wild-type and V599E mutant BRAF activity in vitro. In addition, BAY 43-9006 demonstrated significant activity against several receptor tyrosine kinases involved in neovascularization and tumor progression, including vascular endothelial growth factor receptor (VEGFR)-2, VEGFR-3, platelet-derived growth factor receptor beta, Flt-3, and c-KIT. In cellular mechanistic assays, BAY 43-9006 demonstrated inhibition of the mitogen-activated protein kinase pathway in colon, pancreatic, and breast tumor cell lines expressing mutant KRAS or wild-type or mutant BRAF, whereas non-small-cell lung cancer cell lines expressing mutant KRAS were insensitive to inhibition of the mitogen-activated protein kinase pathway by BAY 43-9006. Once daily oral dosing of BAY 43-9006 demonstrated broad-spectrum antitumor activity in colon, breast, and non-small-cell lung cancer xenograft models. Immunohistochemistry demonstrated a close association between inhibition of tumor growth and inhibition of the extracellular signal-regulated kinases (ERKs) 1/2 phosphorylation in two of three xenograft models examined, consistent with inhibition of the RAF/MEK/ERK pathway in some but not all models. Therefore, if a BRAF mutation is detected, a BRAF inhibiting composition can be used in treatment.

Also disclosed are methods of determining treatment type for a subject with cancer, comprising a) testing a sample from the subject for microsatellite stability; b) testing a sample from the subject for a BRAF mutation; c) analyzing results from steps a) and b), and d) determining the treatment type based on step c). As disclosed above, the stage of the cancer can be determined, and together with the results of step a) and b), can be used to determine how to treat the subject.

The disclosed compositions can be used in a variety of ways as research tools. For example, the disclosed compositions can be used to study the interactions between BRAF and microsatellite stable tumors, by for example acting as inhibitors of binding. The compositions can be used for example as targets in combinatorial chemistry protocols or other screening protocols to isolate molecules that possess desired functional properties related to BRAF and microsatellite stable tumors. The disclosed compositions can also be used diagnostic tools related to cancer.

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any method for determining allelic analysis of for example, BRAF, particularly allelic analysis as it relates to BRAF and functions. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

2. Methods of Gene Modification and Gene Disruption

The disclosed compositions and methods can be used for targeted gene disruption and modification in any animal that can undergo these events. Gene modification and gene disruption refer to the methods, techniques, and compositions that surround the selective removal or alteration of a gene or stretch of chromosome in an animal, such as a mammal, in a way that propagates the modification through the germ line of the mammal. In general, a cell is transformed with a vector which is designed to homologously recombine with a region of a particular chromosome contained within the cell, as for example, described herein. This homologous recombination event can produce a chromosome which has exogenous DNA introduced, for example in frame, with the surrounding DNA. This type of protocol allows for very specific mutations, such as point mutations, to be introduced into the genome contained within the cell. Methods for performing this type of homologous recombination are disclosed herein.

One of the preferred characteristics of performing homologous recombination in mammalian cells is that the cells should be able to be cultured, because the desired recombination event occur at a low frequency.

Once the cell is produced through the methods described herein, an animal can be produced from this cell through either stem cell technology or cloning technology. For example, if the cell into which the nucleic acid was transfected was a stem cell for the organism, then this cell, after transfection and culturing, can be used to produce an organism which will contain the gene modification or disruption in germ line cells, which can then in turn be used to produce another animal that possesses the gene modification or disruption in all of its cells. In other methods for production of an animal containing the gene modification or disruption in all of its cells, cloning technologies can be used. These technologies generally take the nucleus of the transfected cell and either through fusion or replacement fuse the transfected nucleus with an oocyte which can then be manipulated to produce an animal. The advantage of procedures that use cloning instead of ES technology is that cells other than ES cells can be transfected. For example, a fibroblast cell, which is very easy to culture can be used as the cell which is transfected and has a gene modification or disruption event take place, and then cells derived from this cell can be used to clone a whole animal.

3. Method of Treating Cancer

The disclosed compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Compounds disclosed herein may also be used for the treatment of precancer conditions such as cervical and anal dysplasias, other dysplasias, severe dysplasias, hyperplasias, atypical hyperplasias, and neoplasias.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Materials and Methods
Study Population.
Study participants were White, Black, or Hispanic and were from either the Kaiser Permanente Medical Care Program (KPMCP) of northern California or an eight-county area in Utah (Davis, Salt Lake, Utah, Weber, Wasatch, Tooele, Morgan, and Summit counties). Eligibility criteria for cases included diagnosis with first-primary incident colon cancer (International Classification of Diseases for Oncology, Second Edition codes 18.0 and 18.2-18.9) between Oct. 1, 1991 and Sep. 30, 1994 and ages between 30 and 79 years at time of diagnosis. Cases with cancers of the rectosigmoid junction or rectum (defined as the first 15 cm from the anal opening) or with known familial adenomatous polyposis, ulcerative colitis, or Crohn's disease were not eligible. All cases were adenocarcinomas or carcinomas. This study population is part of a previously described sample (Slattery et al. Cancer Res 57:75-80 (1997)). Tumor blocks and amplifiable DNA was originally available on 1,530 individuals, and sufficient DNA for determination of the BRAF V600E mutation was available on tumors from 911 individuals. This group did not differ from the original sample with respect to age, gender, American Joint Committee on Cancer (AJCC) stage, histologic differentiation, tumor site, prognosis, or family history of colorectal cancer.

Information on age at time of diagnosis, sex, tumor site, and tumor stage were available from the Northern California Tumor Registry, Sacramento Tumor Registry, and Utah Cancer Registry. These registries are members of the Surveillance, Epidemiology, and End Results program. Proximal tumors were defined as cecum through transverse colon; tumors in the splenic flexure, descending, and sigmoid colon were defined as distal. Tumors were staged by AJCC criteria (American Joint Committee on Cancer. AJCC Cancer Staging Manual. 5th ed. Philadelphia: Lippincott-Raven (1997)). Vital status, date of death, primary cause of death, and two contributing causes of death were obtained from local tumor registries using death certificate information. Active follow-up of people diagnosed with cancer is done through the cancer registries on a continuous basis. Vital status as of Dec. 30, 1998 was obtained for all study participants. For individuals whose vital status or cause of death could not be determined through local tumor registries, National Death Index tapes were used. Months of survival were calculated by subtracting the date of last contact or death from the date of diagnosis. Deaths from any cause as well as deaths attributed to colon cancer were assessed. Family history of cancer information was collected as part of an interviewer-administered questionnaire. Study participants were asked to list first names of all first-degree blood relatives, including parents, siblings, and children. For each family member enumerated, it was determined if that person ever had been diagnosed with cancer, age at diagnosis, and type of cancer. All aspects of this study were approved by the University of Utah and KPMCP institutional review boards.

BRAF V600E Mutation Detection.
The BRAF V600E mutations have been determined in a previous study. Briefly, exon 15 of BRAF was amplified from DNA previously extracted from microdissected tumors (Samowitz et al. (2001)) using the forward primer 5V-TCATAATGCTTGCTCTGATAGGA-3V (SEQ ID NO: 1) and the reverse primer 5V-CTTTCTAGTAACTCA-GCAGC-3V (SEQ ID NO: 2). Amplifications were carried out using AmpliTaq Gold and a PCR profile consisting of a 9-minute initial denaturation at 95° C. followed by 35 cycles of 20 seconds at 95° C. 20 seconds at 60° C., and 30 seconds at 72° C. with a 5-minute final extension at 72° C. Mutations were verified by sequencing in both directions. Sufficient DNA was available for analysis of 919 tumors. Mutations other than the V600E mutation were identified in 4 tumors but were not used in any of the statistical analyses.

TABLE 1

Comparison of BRAF V600E mutated to BRAF WT in microsatellite-stable and microsatallite-unstable colon cancers with respect to clinicopathologic variables ad tumor mutations

| | Stable | | | Unstable | | |
|---|---|---|---|---|---|---|
| | BRAF WT, n (%) | BRAF mutant, n (%) | OR* (95% CI) | BRAF WT, n (%) | BRAF mutant, n (%) | OR* (95% CI) |
| Tumor site | | | | | | |
| Proximal | 328 (44.4) | 27 (69.2) | 1.00 (Reference) | 33 (92.5) | 37 (91.5) | 1.00 (Reference) |
| Distal | 410 (55.6) | 12 (30.8) | 0.36 (0.18-0.71) | 7 (17.5) | 3 (7.5) | 0.38 (0.09-1.60) |
| AJDC stage[1] | | | | | | |
| 1 | 192 (25.5) | 1 (2.5) | | 8 (20.0) | 8 (19.0) | 1.00 (Reference) |
| 2 | 208 (27.6) | 6 (15.0) | 1.00 (Reference) | 19 (47.5) | 12 (28.6) | 0.63 (0.19-2.13) |
| 3 | 214 (28.4) | 19 (47.5) | 5.07 (2.10-12.26) | 11 (27.5) | 19 (45.2) | 1.73 (0.51-5.91) |
| 4 | 139 (18.5) | 14 (35.0) | 5.76 (2.28-14.55) | 2 (5.0) | 3 (7.1) | 1.50 (0.20-11.54) |
| $P_{trend}$ | | | <0.0001 | | | 0.22 |
| Age[2] | | | | | | |
| <55 | 100 (13.1) | 6 (15.0) | 1.00 (Reference) | 13 (3.25) | 1 (2.3) | |
| 56-64 | 197 (25.8) | 14 (35.0) | 1.18 (0.44-3.18) | 6 (15.0) | 5 (11.6) | 1.00 (Reference) |
| 65-70 | 189 (24.8) | 10 (25.0) | 0.88 (0.31-2.50) | 5 (22.5) | 13 (30.2) | 8.23 (2.07-32.75) |
| 71-79 | 277 (36.3) | 10 (25.0) | 0.60 (0.21-1.70) | 16 (40.0) | 24 (55.8) | 4.75 (1.56-14.48) |
| $P_{trend}$ | | | 0.16 | | | 0.009 |

TABLE 1-continued

Comparison of BRAF V600E mutated to BRAF WT in microsatellite-stable and microsatallite-unstable colon cancers with respect to clinicopathologic variables ad tumor mutations

| | Stable | | | Unstable | | |
|---|---|---|---|---|---|---|
| | BRAF WT, n (%) | BRAF mutant, n (%) | OR* (95% Cl) | BRAF WT, n (%) | BRAF mutant, n (%) | OR* (95% Cl) |
| Gender | | | | | | |
| Male | 419 (54.9) | 16 (40.0) | 1.00 (Reference) | 20 (50.0) | 18 (41.9) | 1.00 (Reference) |
| Female | 344 (45.1) | 24 (60.0) | 1.83 (0.96-3.49) | 20 (50.0) | 25 (28.1) | 1.39 (0.58-3.30) |
| Differentiation[3] | | | | | | |
| Well | 71 (10.1) | 2 (5.3) | | 3 (3.1) | 1 (2.4) | |
| Moderate | 526 (74.6) | 23 (60.5) | 1.00 (Reference) | 20 (51.2) | 23 (54.8) | 1.00 (Reference) |
| Poor | 108 (15.3) | 13 (34.2) | 2.87 (1.43-5.79) | 14 (37.8) | 18 (42.9) | 1.23 (0.50-3.04) |
| Mucinous Histology | | | | | | |
| No | 685 (89.5) | 30 (75.0) | 1.00 (Reference) | 29 (72.5) | 28 (66.7) | 1.00 (Reference) |
| Yes | 78 (10.2) | 10 (25.0) | 2.93 (1.38-6.22) | 11 (27.5) | 14 (33.3) | 1.32 (0.51-3.39) |
| Colorectal family history[4] | | | | | | |
| NO | 284 (79.6) | 9 (47.4) | 1.00 (Reference) | 83 (59.1) | 17 (68.0) | 1.00 (Reference) |
| Yes | 73 (20.4) | 10 (52.6) | 4.23 (1.65-10.84) | 9 (40.9) | 8 (32.0) | 0.64 (0.18-2.19) |
| Ki-ras | | | | | | |
| WT | 458 (63.6) | 37 (97.4) | 1.00 (Reference) | 27 (75.0) | 43 (000.0) | |
| Mutant | 262 (36.4) | 1 (2.6) | 0.05 (<0.01-0.35) | 9 (25.0) | 0 (0.0) | |
| p53 | | | | | | |
| WT | 369 (51.0) | 21 (58.8) | 1.00 (Reference) | 35 (89.7) | 36 (85.7) | 1.00 (Reference) |
| Mutant | 355 (49.0) | 18 (46.2) | 0.89 (0.47-1.70) | 4 (10.3) | 6 (14.3) | 1.46 (0.38-5.61) |
| CIMP | | | | | | |
| Low | 554 (78.7) | 3 (8.6) | 1.00 (Reference) | 11 (32.4) | 2 (4.7) | 1.00 (Reference) |
| High | 150 (21.3) | 32 (91.4) | 39.39 (11.90-130.41) | 23 (67.6) | 42 (95.3) | 9.80 (2.00-48.10) |

*OR for BRAF mutant status associated with this characteristic, from univariate analysis except as noted.
[1]Stages 1 and 2 were combined in the calcalation of ORs due to small cell size.
[2]The youngest two age groups were combined to allow the calculation of ORs.
[3]Well and moderate differentation were combined in the calcalation of the ORs due to small cell size.
[4]Age adjusted CpG Island Methylator Phenotype.

CIMP had been determined in a previous study. Briefly, sodium bisulfate modification was done on DNA extracted from tumors microdissected for previous studies (Samowitz et al. (2001)). Methylation-specific PCR was then done as described previously for the following CpG islands: MINT 1, MINT 2, MINT 31, p16, and hMLH1 (Park et al. Am J Pathol 162: 815-22 (2003)). This panel was being used at the time our study began by the group that originally described CIMP and its importance in colorectal cancer, and their criterion for CIMP high was methylation of two or more of these CpG islands (Park et al. (2003), Frazier et al. Cancer Res 63:4805-8 (2003)). CIMP low was defined as less than two of five markers methylated. Sufficient DNA for CIMP determination was present for 838 tumors with BRAF V600E results and 26 tumors without BRAF V600E results.

Ki-Ras, p53, and Microsatellite Instability.

Codon 12 and 13 Ki-ras mutations, p53 mutations in exons 5 to 8, and MSI were determined in previous studies (Samowitz et al. (2001), Samowitz et al. Int J Cancer 99:597-602 (2002), Samowitz et al. Cancer Epidemiol Biomarkers Prev 9:1193-7 (2000)). These studies preceded the development of the Bethesda consensus panel; the MSI markers used were BAT-26 (a mononucleotide repeat, which by itself is a very good measure of generalized instability), TGFbRII (a coding mononucleotide repeat, which is unstable in most colorectal cancers with MSI), and a panel of 10 tetranucleotides repeats, which show a high correlation with the Bethesda consensus panel and BAT-26 (Samowitz et al. Am J Pathol 158:1517-24 (2001)). A hierarchical approach was then used for MSI determination; 824 tumors were classified (either stable or unstable) for BAT-26, 59 tumors (which did not show results for BAT-26) were classified using TGFbRII, and 3 tumors (which showed no results for either BAT-26 or TGFbRII) were classified using the panel of 10 tetranucleotide repeats; in that case, if z30% of the 10 tetranucleotide repeats were unstable, the tumor was classified as unstable, and if <30% were unstable, the tumor was classified as stable. MSI could not be determined for 25 tumors.

Statistical Analysis.

Univariate relationships between BRAF V600E mutation and age at diagnosis, tumor site, AJCC stage, gender, grade of differentiation, a histologic classification of mucinous, mucin-producing, or signet ring, family history of colorectal cancer (defined as colorectal cancer in a first-degree relative), mutations in Ki-ras and p53, and CIMP were evaluated using logistic regression to calculate odds ratios (OR). All Ors were unadjusted, except for family history of colorectal cancer, which was adjusted for age at diagnosis. Survival data were available for 930 individuals with CIMP and/or BRAF results; 905 of these had BRAF mutational data and 857 of these had CIMP data. Five-year survival was evaluated using Kaplan-Meier plots for mortality due to all causes. Associations and interactions between BRAF, CIMP, and survival were evaluated among microsatellite-stable tumors using Cox proportional hazards models adjusting for age at diagnosis, AJCC stage, and tumor site. Median follow-up time was 65 months. All data analyses were done using SAS version 8.2 (SAS Institute, Cary, N.C.).

Results

BRAF and Microsatellite-Stable Cancers.

The V600E BRAF mutation was detected in 9.5% (87 of 911) of colon cancers overall and 5% (40 of 803) of microsatellite-stable cancers. Relationships between BRAF V600E mutation and clinicopathologic variables and tumor mutations in microsatellite-stable tumors are shown in Table XXX. Significant relationships were seen between the V600E BRAF mutation and CIMP high, family history of colorectal cancer [OR, 4.23; 95% confidence interval (95% CI), 1.65 10.84], Ki-ras wildtype (WT), higher AJCC stage, poor differentiation, mucinous histology, and proximal tumor location. A nonsignificant excess of BRAF mutations was observed for females. The relationship to CIMP high was particularly strong (OR, 39.39; 95% CI, 11.90-130.41), as 91.4% of BRAF mutated tumors were CIMP high compared with 21.3% of BRAF WT. BRAF and Ki-ras mutations were, with one exception, mutually exclusive. BRAF mutations were not related to increased age.

BRAF and Microsatellite-Unstable Cancers.

The BRAF V600E mutation was seen in 51.8% (43 of 83) of microsatellite-unstable cancers. The comparison of the V600E BRAF mutation to BRAF WT with respect to clinicopathologic variables and tumor mutations in microsatellite-unstable tumors is shown in Table 1. Unstable tumors with the V600E BRAF mutation clearly show the same relationship as microsatellite-stable mutant tumors with respect to CIMP high and lack (in this case, complete) of Ki-ras mutations. One difference between unstable BRAF mutated tumors and stable mutated tumors is that unstable tumors with the V600E BRAF mutation were associated with increased age.

Five-Year Survival.

Univariate relationships between several clinicopathologic variables and percent 5-year survival are shown in Table 2. Significant relationships with poor survival were seen with age, proximal tumor site, higher AJCC stage, and poor differentiation, whereas MSI was associated with an improved prognosis. Both the BRAF V600E mutation and CIMP high were associated with a poorer 5-year survival in microsatellite-stable tumors (16.7% and 48.7%, respectively). Among CIMP high microsatellite-stable tumors, the V600E BRAF mutation was associated with a significantly poorer 5-year survival (14.6% versus 55.8%; P<0.0001). Microsatellite-unstable tumors with or without the V600E BRAF mutation were associated with an excellent percent 5-year survival (76.2 and 75.0%, respectively).

TABLE 2

Univariate relationships with 5-year survival

|  | 5-y overall survival (%) |
| --- | --- |
| Age at time of diagnosis | |
| <55 | 58.5 |
| 55-64 | 63.5 |
| 65-70 | 64.8 |
| 71-79 | 52.9 |
| P | 0.02* |
| Gender | |
| Male | 59.0 |
| Female | 59.7 |
| P | 0.98 |

TABLE 2-continued

Univariate relationships with 5-year survival

|  | 5-y overall survival (%) |
| --- | --- |
| Tumor site | |
| Proximal | 55.6 |
| Distal | 63.7 |
| P | <0.01* |
| AJCC stage | |
| 1 | 83.7 |
| 2 | 75.3 |
| 3 | 55.4 |
| 4 | 8.7 |
| P | <0.01* |
| Differentiation | |
| Well | 78.6 |
| Moderate | 60.6 |
| Poor | 46.2 |
| P | <0.01* |
| MSI | |
| Stable | 57.7 |
| Unstable | 75.9 |
| P | <0.01* |
| CIMP | |
| Low | 60.2 |
| High | 55.5 |
| P | 0.12 |
| CIMP (stable) | |
| Low | 60.2 |
| High | 48.7 |
| P | <0.01* |
| CIMP (unstable) | |
| Low | 71.4 |
| High | 74.6 |
| P | 0.77 |
| BRAF | |
| WT | 60.7 |
| Mutant | 47.5 |
| P | <0.01* |
| BRAF (stable) | |
| WT | 60.0 |
| Mutant | 16.7 |
| P | <0.01* |
| BRAF (unstable) | |
| WT | 75.0 |
| Mutant | 76.2 |
| P | 0.89 |

NOTE:
P is a log-rank statistic for differences in 5-year survival.
*Difference in survival rates are statistically significant.

Microsatellite-Stable Tumors, BRAF Mutations, CpG Island Methylator Phenotype, and Survival.

Of the 820 individuals with microsatellite-stable cancers, 342 were no longer living 5 years after diagnosis. 256 died of colon cancer, 29 died of another type of cancer, 47 died of another cause, and the cause of death was unspecified for 10 individuals. The effects of the V600E BRAF mutation and CIMP on the likelihood of dying from all causes in microsatellite-stable tumors are shown in Table 3. BRAF mutated tumors were associated with a significantly higher risk of dying than BRAF WT tumors in an analysis adjusted for age [hazard rate ratio (HRR), 3.97; 95% CI, 2.76-5.71], in an analysis adjusted for age, stage, and tumor site (HRR, 2.97; 95% CI, 2.05-4.32), and in stage-specific, age-adjusted analyses for AJCC stages 2 to 4 (HRRs, 4.88, 3.60, and 2.04, respectively). CIMP high tumors were also associated with a significantly higher HRR in age-adjusted analyses, although the point estimate was lower than for BRAF (1.45 versus 3.97). Adjustment for age, stage, and tumor site eliminated the association of CIMP and survival (HRR, 1.13; 95% CI, 0.87-1.47), and no significant relationships between CIMP high and risk of dying were seen in AJCC stage-specific analyses.

The effects of the V600E BRAF mutation and CIMP on the likelihood of dying from colon cancer (as opposed to death from all causes) in microsatellite-stable tumors are shown in Table 4. The same relationships of the BRAF V600E mutation and increased likelihood of dying are seen as with overall survival in Table 3; indeed, the HRRs are even higher. CIMP high shows similarly minimal (and mostly nonsignificant) associations with increased risk of dying from colon cancer as were seen with death from all causes. Adjustment for family history of colorectal cancer did not significantly alter these results or those above for death from all causes.

TABLE 3

HRRs for risk of dying from all causes comparing microsatellite-stable tumors with and without the V600E BRAF mutation and with and without CIMP high

|  | BRAF | | | CIMP | | |
| --- | --- | --- | --- | --- | --- | --- |
|  | WT (n = 758) deaths/ person-years* | V600E mutant (n = 40) deaths/ person-years | HRR (95% CI) | Low (n = 570) deaths/ person-years | High (n = 186) deaths/ person-years | HRR (96% CI) |
| Age adjusted | 299/2,788 | 33/70 | 3.97 (2.76-5.71) | 223/2,101 | 96/596 | 1.45 (1.14-1.84) |
| Age, AJCC stage, and tumor site adjusted | 299/2,788 | 33/70 | 2.97 (2.05-4.32) | 223/2,101 | 95/596 | 1.13 (0.87-1.47) |
| Age adjusted by AJCC stage |  |  |  |  |  |  |
| 1 | 32/854 | 0/5 | Undefined | 23/686 | 8/120 | 1.77 (0.79-4.00) |
| 2 | 47/889 | 4/17 | 4.88 (1.73-13.76) | 36/676 | 12/171 | 1.25 (0.65-2.40) |
| 3 | 91/802 | 15/38 | 3.60 (2.07-6.25) | 72/554 | 35/253 | 1.00 (0.67-1.51) |
| 4 | 126/203 | 14/10 | 2.04 (1.16-3.59) | 89/150 | 40/52 | 1.31 (0.89-1.92) |

*Person-years is the sum of each person's time at risk (time from diagnosis to death or censoring, maximum of 5 years), in years.

TABLE 4

HRRs for risk of dying of colon cancer comparing microsatellite-stable tumors with and without the V600E BRAF mutation and with and without CIMP high

|  | BRAF | | | CIMP | | |
| --- | --- | --- | --- | --- | --- | --- |
|  | WT (n = 758) deaths/ person-years | V600E mutant (n = 40) deaths/ person-years | HRR (95% CI) | Low (n = 570) deaths/ person-years | High (n = 186) deaths/ person-years | HRR (95% CI) |
| Age adjusted | 220/2,768 | 30/70 | 4.57 (3.11-6.73) | 160/2,101 | 78/996 | 1.70 (1.29-2.23) |
| Age, AJCC stage, and tumor site adjusted | 220/2,788 | 30/70 | 3.19 (2.14-4.75) | 160/2,101 | 78/996 | 1.30 (0.96-1.74) |
| Age adjusted by AJCC stage |  |  |  |  |  |  |
| 1 | 7/854 | 0/5 | Undefined | 5/686 | 2/210 | 1.74 (0.33-9.30) |
| 2 | 27/889 | 3/17 | 5.83 (1.74-19.53) | 20/676 | 9/171 | 1.76 (0.80-3.88) |
| 3 | 70/802 | 13/38 | 4.06 (2.23-7.39) | 52/554 | 30/253 | 1.23 (0.78-1.93) |
| 4 | 114/208 | 14/10 | 2.28 (1.29-1.02) | 81/150 | 37/81 | 1.37 (0.92-2.06) |

TABLE 5

Joint analysis of BRAF and CIMP status and survival of individuals with microsatellite-stable colon cancers

|  |  | Colorectal cancer survival | | Overall survival | |
| --- | --- | --- | --- | --- | --- |
|  | n | Deaths/ person-years | HRR* (95% CI) | Deaths/ person-years | HRR* (95% CI) |
| BRAF[1] |  |  |  |  |  |
| WT | 758 | 220/2,788 | 1.00 (Reference) | 299/2,788 | 1.00 (Reference) |
| Mutant | 40 | 33/70 | 3.11 (2.04-4.74) | 33/70 | 3.06 (2.06-4.54) |

TABLE 5-continued

Joint analysis of BRAF and CIMP status and survival of individuals with microsatellite-stable colon cancers

| | | Colorectal cancer survival | | Overall survival | |
|---|---|---|---|---|---|
| | n | Deaths/ person-years | HRR* (95% CI) | Deaths/ person-years | HRR* (95% CI) |
| CIMP[2] | | | | | |
| Low | 570 | 160/2,201 | 1.00 (Reference) | 223/2,101 | 1.00 (Reference) |
| High | 186 | 78/596 | 0.97 (0.70-1.36) | 95/596 | 0.88 (0.66-1.18) |
| BRAF WT/CIMP low | 549 | 153/2,037 | 1.00 (Reference) | 213/2,037 | 1.00 (Reference) |
| BRAF mutant/CIMP low | 3 | 2/6 | 20.78 (4.85-89.11) | 2/6 | 11.14 (2.66-46.71) |
| BRAF WT/CIMP high | 150 | 53/530 | 1.01 (0.72-1.42) | 66/530 | 0.91 (0.68-1.22) |
| BRAF mutant/CIMP high | 32 | 24/52 | 3.60 (2.29-5.66) | 27/52 | 3.17 (2.08-4.83) |

*Adjusted for age, AJCC stage, and tumor site.
[1]HRR also adjusted for CIMP.
[2]HRR also adjusted for BRAF.

Multivariate analyses of the effect of BRAF mutations adjusted for CIMP high and CIMP high adjusted for BRAF mutations show that the deleterious effects on survival in microsatellite-stable cancers (either overall or colorectal) are entirely attributable to BRAF mutations (Table 5). This is further exemplified by the analysis of the four permutations of BRAF and CIMP (BRAF WT, CIMP low; BRAF mutant, CIMP low; BRAF WT, CIMP high; and BRAF mutant, CIMP high) and their effect on survival (Table 5); again, it is mutant BRAF rather than CIMP high that increases the risk of death.

Kaplan-Meier survival estimates comparing the overall survival of V600E BRAF mutation versus BRAF WT for microsatellite-stable colon cancers are shown in FIG. 1. Although relatively few numbers of tumors are present at each stage, tumors with the V600E BRAF mutations had a significantly higher risk of death than BRAF WT tumors for stages 2 to 4 (P<0.01, log-rank test).

Figure 2:
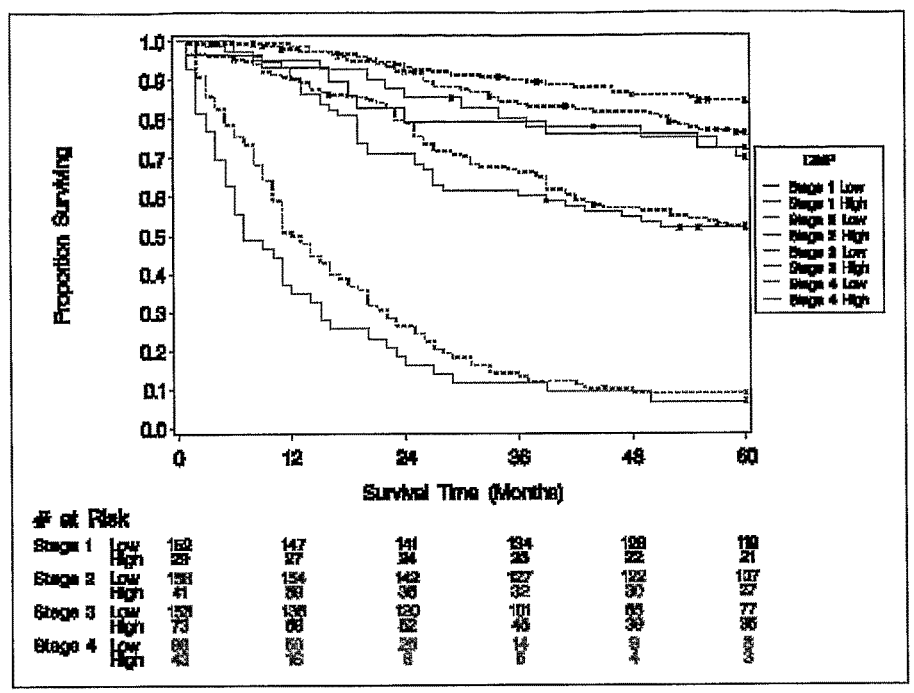
FIG. 2 shows the Kaplan-Meier survival estimates comparing the overall survival of CIMP high and CIMP low for microsatellite-stable tumors.
Figure 3:
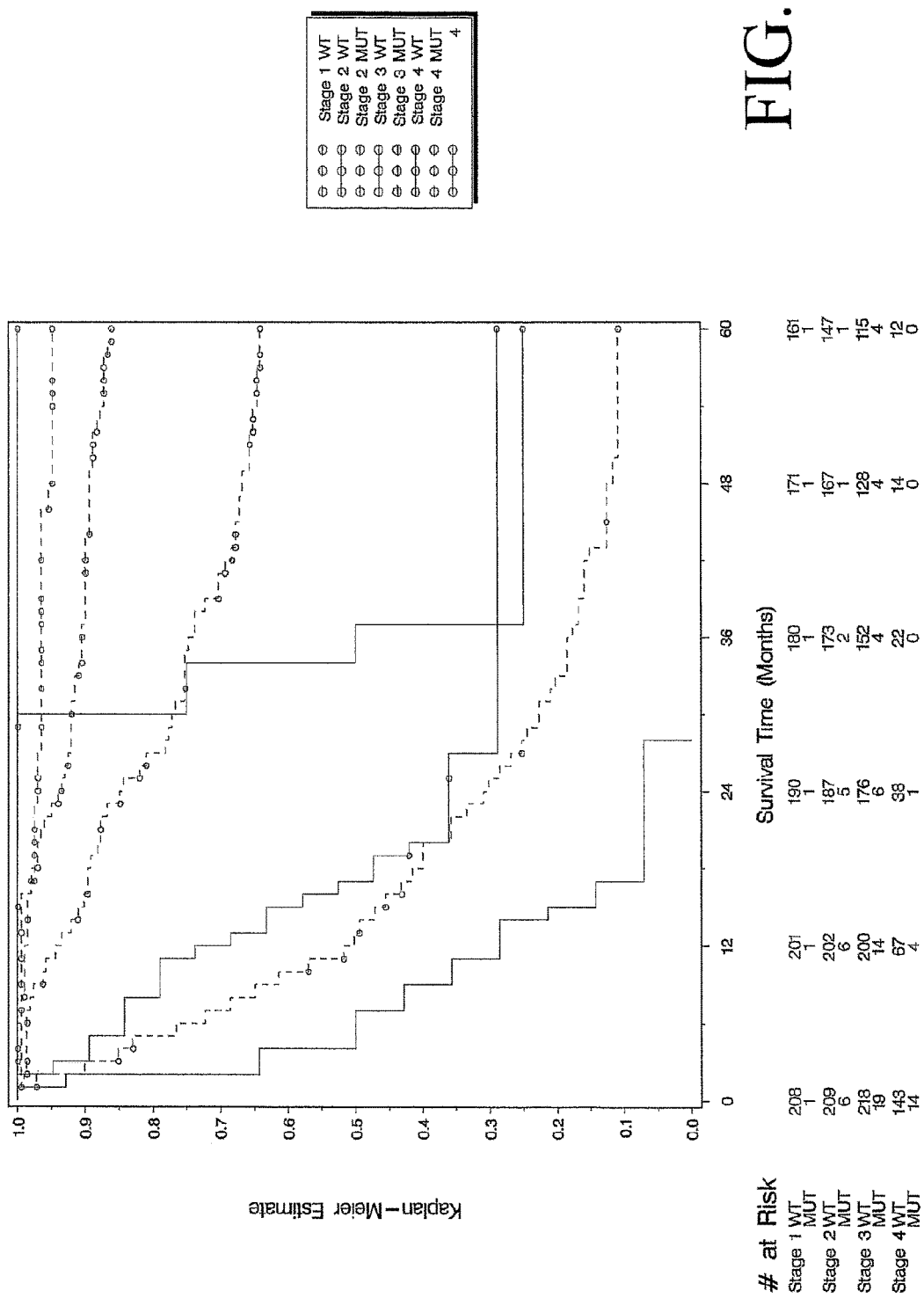
FIG. 3 shows Kaplan-Meier survival estimates of stable colon cancer by stage and BRAF.

The Kaplan-Meier survival estimates comparing the overall survival of CIMP high and CIMP low for microsatellite-stable tumors is shown in FIG. 2. Significant relationships were not seen for any AJCC stage (P=0.09, 0.40, 0.73, and 0.14 for stages 1-4, respectively).

Microsatellite-Unstable Cancers.

Of the 83 individuals with microsatellite-unstable colon cancers, 8 died of colon cancer, 3 died of another type of cancer, 6 died of another cause, and the cause of death was unspecified for 3 individuals. HRRs and Kaplan-Meier survival estimates for microsatellite-unstable tumors with and without the BRAF V600E mutation were not calculated because so few colon cancer deaths (3 and 5, respectively) occurred in these groups.

Other BRAF Mutations.

Four other BRAF mutations were identified (Table 6) but were not used in the above analyses. Three of the mutations occurred in codon 594 (D594N, D594G, and D594G) and were present in microsatellite-stable, CIMP low tumors. All of these individuals survived at least 5 years (although all were relatively low-stage tumors). The fourth mutation G606R) occurred in a microsatellite-stable, CIMP high tumor and was associated with death due to colon cancer after 19 months.

DISCUSSION

Over 90% of colon cancers with the BRAF V600E mutation were CIMP high (Table 1). In microsatellite-stable cancers, tumors with the V600E mutation also showed many of the same clinicopathologic relationships observed previously in CIMP high colon cancers in general, including proximal tumor location, increased AJCC stage, poor differentiation, and mucinous histology (Table 1). The major difference was that the V600E BRAF mutation was not related to increased age in stable tumors; several previous studies have noted a relationship between CIMP high and older age in stable tumors (van Rijnsoever et al. *Gut* 51:797-802 (2002), Hawkins et al. *Gastroenterology* 122: 1376-87 (2002)). The relationship between CIMP high and older age remains in the data set if BRAF mutated tumors are excluded. Another potential difference is the impressively increased risk of a positive family history of colorectal cancer associated with the BRAF V600E mutation in microsatellite-stable cancers (OR, 4.23; 95% CI, 1.65-10.84). There has been recent study that related BRAF mutations to colorectal cancer-prone families whose tumors exhibited varying degrees of MSI (Young et al. *Clin Gastroenterol Hepatol* 3:254-63 (2005)), so there is precedence for a relationship between BRAF mutations and family history of colon cancer (although the relationship we observed was only with microsatellite-stable tumors). In two previous studies of CIMP and family history of all types of cancer, one showed a significant relationship (Frazier et al. (2003)) and the other showed a nonsignificant trend, which apparently disappeared in a multivariate analysis (Ward et al. *Cancer Res* 64:7618-21 (2004)); a small but nonsignificant relationship between CIMP high and family history of colorectal cancer and no relationship between CIMP and all types of cancer have been shown.

Finally, another difference is that stable tumors with the V600E BRAF mutation did not show the increased frequency of Ki-ras mutations that we and others have reported with CIMP in stable tumors; this is not surprising given that these mutations are, for the most part, mutually exclusive (Table 1; Rajagopalan et al. (2002), Kambara et al. (2004)).

In contrast with stable tumors, the V600E BRAF mutation shows the relationship to increased age typically exhibited by CIMP high colon cancer (Hawkins et al. (2002)).

The V600E BRAF mutation was present in 5% (40 of 803) of microsatellite-stable colon cancers and was associated with a significantly worse survival than microsatellite-stable tumors without this mutation. This was true in a univariate analysis after adjustment for age, stage, and tumor site, in stage-stratified analyses for AJCC stages 2 to 4, and in a Kaplan-Meier analysis for stages 2 to 4 (Tables 2, 3, and 4; FIG. 1). Because >90% of microsatellite-stable tumors with the V600E BRAF mutation are also CIMP high, it is important to see whether this poorer survival was specifically related to this mutation or whether it was simply a function of CIMP. Although CIMP high stable tumors were associated with a significantly worse 5-year survival than CIMP low stable tumors in univariate and age-adjusted analyses, the effect of CIMP high on survival was less than that seen with BRAF (Tables 2 and 3). In addition, and in contrast to the BRAF V600E mutation, no significant relationships were seen for CIMP in either an analysis adjusted for age, stage, and tumor site, in stage-stratified analyses, or in a Kaplan Meier analysis (Table 3; FIG. 2). The relatively minor effects of CIMP high on survival suggest that the effect of the V600E mutation on survival in stable tumors is not dependent on CIMP. In a direct comparison of CIMP high stable tumors with and without the V600E mutation, tumors with the V600E mutation had a significantly worse 5-year survival (14.6% versus 55.8%; P<0.0001), and in multivariate analyses of CIMP and BRAF, only BRAF mutations had an effect on survival (Table 5).

The V600E mutation did not have the same effect on survival in tumors with MSI, as unstable tumors with and without this mutation were associated with an excellent 5-year survival (76.2% and 75.0%, respectively). This emphasizes that it is not the V600E mutation per se that confers a poor prognosis but rather that the mutation has different effects depending on the genetic background in which it occurs and/or, perhaps, the oncogenic pathway that led to the development of the cancer. It should be stressed that this difference is not due to the presence or absence of CIMP, as >90% of both microsatellite-unstable and microsatellite-stable tumors with the V600E BRAF mutation are CIMP high (Table 1).

Microsatellite-unstable colorectal cancers can develop from a subset of hyperplastic polyps (which often have BRAF mutations and are CIMP high) rather than from traditional adenomas (Kambara et al. (2004)). It is possible that microsatellite-stable tumors with BRAF mutations develop from a different pathway (e.g., adenomas with BRAF mutations; Rajagopalan et al. (2002)) or that both develop from the same serrated, hyperplastic polyp pathway but diverge with respect to clinical aggressiveness with the methylation of hMLH1 in a subset of tumors that then develop MSI.

Four other BRAF mutations were identified (Table 5). Three of them encode substitutions of uncharged for charged amino acids at codon 594. A similar mutation (D594V) has been shown to lead to impaired kinase activity of BRAF and loss of the ability to activate extracellular signal-regulated kinase (Wan et al. *Cell* 116:855-67 (2004)). Interestingly, all three of these mutations occurred in CIMP low tumors and all three individuals survived at least 5 years (although all were relatively low stage tumors). The fourth mutation (G606R) is similar to other activating mutations described by Wan et al. (including the V600E mutation) in that it occurred in the activation segment of the protein and was a substitution of a charged for an uncharged amino acid. This mutation occurred in a microsatellite-stable, CIMP high tumor and the individual died of colon cancer after 19 months, similar to the CIMP high context, increased stage, and poor survival we have seen with the more common V600E mutation.

The findings with respect to the deleterious effect of BRAF mutations in microsatellite-stable cancers have important clinical implications. Individuals with such tumors can be treated more aggressively, including those with stage II cancers who typically do not receive chemotherapy at the present time. Specific therapies can also be used for these tumors.

In summary, the large population-based study (Example 1) showed that microsatellite-stable colon cancers with the V600E BRAF mutation differed from other CIMP high stable tumors by showing no relationship with increased age and by showing a strong relationship to a family history of colorectal cancer. In addition, microsatellite-stable tumors with BRAF mutation had significantly worse overall stable tumors without this mutation and specifically poorer survival in AJCC stages 2 to 4. This poor survival related to the CIMP high phenotype, and the V600E not affect the excellent prognosis of microsatellite-carcinomas.

2. Example 2

A large population-based sample of individuals with colon cancer were evaluated, and univariate and multivariate analyses of CIMP with clinicopathologic variables and tumor mutations were used to determine the biologic relevance of this phenotype. 864 tumors from individuals with colon cancer from Utah and Northern California were evaluated by methylation-specific PCR of CpG islands in hMLH1, MINT 1, MINT 2, MINT 31 and CDKN2A (p16). CIMP high was defined as methylation at two or more of these loci. The BRAF V600E mutation was determined by sequencing. Microsatellite instability had been determined previously. Results: In a multivariate analysis of microsatellite stable tumors, CIMP high was significantly related to the V600E BRAF mutation (OR 39.52, 95% C.I. 11.44, 136.56), KRAS2 mutations (OR 2.22, 95% C.I. 1.48, 3.34), older age (p trend=0.03), and increased stage (p trend=0.03), and these tumors were less likely to be located in the distal colon (OR 0.42, 95% C.I. 0.27, 0.65). CIMP high unstable tumors were also more likely to have the V600E BRAF mutation, be proximally located, and occur in older individuals (in univariate analyses). However, CIMP high unstable tumors were significantly more likely than their stable counterparts to be KRAS2 wild type, TP53 wild type, poorly differentiated, proximally located, occur at lower stages, and have the BRAF V600E mutation (64.1% vs. 17.6%). Conclusions: Evaluation of a large, population-based sample strongly supports the biologic relevance of CIMP in colon cancer. However, the presence or absence of microsatellite instability has a major effect on the expression of this phenotype.

Study Population. Study participants were white, black, or Hispanic and were from either the Kaiser Permanente Medical Care Program (KPMCP) of Northern California or an eight county area in Utah (Davis, Salt Lake, Utah, Weber, Wasatch, Tooele, Morgan, and Summit counties). Eligibility criteria for cases included diagnosis with first-ID primary incident colon cancer (ICD-0 2nd edition codes 18.0, 18.2 to 18.9) between Oct. 1, 1991 and Sep. 30, 1994, age between 30 and 79 years at time of diagnosis, and mentally competent to participate in the study. Cases with cancers of the rectosigmoid junction or rectum (defined as the first 15 cm from the anal opening) or with known familial adenomatous polyposis, ulcerative colitis, or Crohn's disease were not eligible. All cases were adenocarcinomas or carcinomas. This study population is part of a previously described sample. Tumor blocks and amplifiable DNA were originally available on 1530 individuals, and this represents 84% of all individuals diagnosed with colon cancer, making this a truly population-based sample. This sample has been used for previous population-based studies on KRAS2, TP53 and microsatellite instability. Sufficient DNA for determination of CIMP (which required a fairly large aliquot of DNA) was available on tumors from 864 individuals. This group did not differ from those for whom CIMP was not determined with respect to age, AJCC stage, histologic differentiation, tumor site, prognosis, or family history of colorectal cancer.

Proximal tumors were defined as cecum through transverse colon; tumors in the splenic flexure, descending, and sigmoid colon were defined as distal. Tumors were staged according to American Joint Committee on Cancer (AJCC) criteria and histologic grade and presence or absence of mucinous histology was determined by reviewing pathology reports. Since we did not have access to complete medical records, AJCC stage IV tumors were identified by using SEER summary stage codes to determine whether or not distant metastases were present. All aspects of this study were approved by the University of Utah and KPMCP Institutional Review Boards.

CpG island methylator phenotype (CIMP) Sodium bisulfate modification was performed on DNA extracted from tumors microdissected for previous studies. Methylation-specific PCR was then performed as described previously for the following CpG islands: MINT 1, MINT 2, MINT 31, CDKN2A(p16), and hMLH1(16). This panel was being used at the time the study began by the group which originally described CIMP and its importance in colorectal cancer, and their criterion for CIMP high was methylation of two or more of these CpG islands. Methylation was defined as a recognizable band on an agarose gel using the methylation-specific primers. CIMP low was defined as less than two of five markers methylated. The primers used for hMLH1 methylation as part of the CIMP panel are located approximately 170 and 270 base pairs five prime of the start codon. hMLH1 methylation was also determined using a different set of primers located approximately 650-800 base pairs five prime to the start codon, but this result was not used for the determination of CIMP high and low.

BRAF V600E mutation detection: The BRAF V600E mutation was detected by amplifying exon 15 of BRAF using the forward primer 5'-TCA TAA TGC TTG CTC TGA TAG GA-3' (SEQ ID NO: 3) and the reverse primer 5'-CTT TCT AGT AAC TCA GCA GC-3' (SEQ ID NO: 4). Amplifications were carried out using AmpliTaq Gold and a PCR profile consisting of a 9-minute initial denaturation at 95° C., then 35 cycles of 20 s at 95° C., 20 s at 60° C., and 30 s at 72° C. with a 5 minute final extension at 72° C. Mutations were verified by sequencing in both directions.

KRAS2, TP53, and microsatellite instability: Codon 12 and 13 KRAS2 mutations, TP53 mutations in exons 5-8, and microsatellite instability were determined in previous studies. These studies preceded the development of the Bethesda consensus panel; the microsatellite instability markers used were BAT-26 (a mononucleotide repeat which by itself is a very good measure of generalized instability, TGFβRII (a coding mononucleotide repeat which is unstable in most colorectal cancers with microsatellite instability) and a panel of 10 tetranucleotide repeats which show a high correlation with the Bethesda consensus panel and BAT-26. A hierarchical approach was then used for microsatellite instability determination. 784 tumors were classified (either stable or unstable) for BAT-26. tumors (which did not show results for BAT-26) were classified using TGFβRII and three tumors (which showed no results for either BAT-26 or TGFβRII) were classified using the panel of 10 tetranucleotide repeats; in that case, if 30% or more of the 10 tetranucleotide repeats were unstable, the tumor was classified as unstable, and if less than 30% were unstable the tumor was classified as stable. Microsatellite instability data was available on 840 of the 864 tumors evaluated by CIMP.

Statistical analysis: Differences in the proportion of microsatellite stable and unstable tumors in those tumors classified as CIMP high or with hMLH1 methylation (using the two sets of primers described above under CIMP (16, 17)) were evaluated using $\chi 2$ statistics. Univariate relationships between CIMP and age, tumor site, AJCC stage, gender, differentiation, a positive histologic classification of mucinous, mucin-producing or signet ring, KRAS2mutations, TP53 mutations, and the BRAF V600E mutation were evaluated using logistic regression to calculate crude odds ratios. Multivariate logistic regression was used to calculate adjusted odds for each of the above measures in microsatellite stable cancers. One multivariate model adjusted for age, tumor site, AJCC stage, gender, differentiation, and histology, and the other multivariate model adjusted for all of these measures plus tumor mutations. Family history of cancer in first degree relatives was limited to those subjects that participated in the interview and so it was adjusted for age and evaluated independently of the other measures.

Results: CIMP and Microsatellite instability: CIMP high was observed in 256 of 864 tumors (29.6%). 250 of the 840 colon carcinomas for which microsatellite instability data was available were CIMP high (29.8%, Table 1). 762 of the cancers were microsatellite stable and 78 were unstable. Unstable tumors were significantly more likely to be CIMP high than stable tumors (82.1% vs. 24.4%, p<0.0001). Representative examples of CpG island methylation in CIMP high and CIMP low colon cancers are shown herein. hMLH1 methylation as determined by the original primers used by Herman et al (see Methods above) was seen in 21.3% of tumors overall, 15.3% of microsatellite stable tumors (66% of which were CIMP low, data not shown in tables) and 80.2% of unstable tumors. hMLH1 methylation as determined by the primers used by Park et al. (see Methods above) was more specific for unstable tumors but less sensitive, as it was seen in 2.1% of stable and 72.5% of unstable tumors. Regardless of the methylation measurement, however, significantly more hMLH1 methylation was seen in unstable tumors than in stable tumors. Examples of the relative non-specificity of hMLH1methylation as determined by the primers used by Herman et al for microsatellite instability and CIMP high are shown herein.

Microsatellite stable tumors and CIMP: The relationship between CIMP and clinicopathologic variables and tumor mutations for microsatellite stable tumors is shown in herein. In univariate analyses there were significant relationships with the BRAF V600E mutation, mutant KRAS2, proximal site, higher AJCC stage, increased age, poor differentiation, and mucinous histology. There was a trend towards a relationship with wild type TP53, but this was not statistically significant. No significant relationship to gender was seen. The relationship with the BRAF V600E mutation was particularly notable, as it was seen in 17.6% of CIMP high tumors and only 0.5% of CIMP low tumors (OR 39.40, 95% C.I. 11.90, 130.42). A multivariate analysis was then performed using all clinicopathologic variables except tumor mutations. In this analysis all of the previous univariate relationships were seen. Finally, a multivariate analysis which included tumor mutations showed significant relationships with the BRAF V600E mutation, KRAS2 mutations, proximal location, older age, and increased stage, as well as non-significant trends towards poor differentiation and mucinous histology. Again, the relationship with the BRAF V600E mutation was highly significant (OR 39.52, 95% C.I. 11.44, 136.56).

Microsatellite unstable tumors and CIMP: The relationship between CIMP and clinicopathologic variables and tumor mutations for unstable tumors is shown herein. When compared to CIMP low unstable tumors, CIMP high unstable tumors had significantly more BRAF V600E mutations, were more likely to be proximal, occurred in older individuals, and were less likely to have KRAS2 mutations. Individuals with unstable CIMP high tumors also were more likely to be women and have tumors with poor differentiation, but these relationships were not statistically significant. Once again, the relationship between CIMP high and the BRAF V600E mutation was particularly striking (OR 9.80, 95% C.I. 2.00, 48.12). Multivariate analyses could not be performed in unstable tumors due to their relatively small numbers.

CIMP high unstable vs. CIMP high stable tumors: A direct comparison of CIMP high unstable tumors with CIMP high stable tumors is shown. Unstable CIMP high tumors were significantly more likely to be KRAS2 wild type, TP53 wild type, BRAF mutated (64.1% vs. 17.6%), proximal, low stage, and poorly differentiated. There was a trend towards CIMP high unstable tumors occurring more often in women and being more likely to have a mucinous histology than CIMP high stable tumors, but these did not quite reach statistical significance. Since hMLH1 methylation is very common in unstable tumors and very rare in stable tumors (Table 1), we also compared stable and unstable tumors using a CIMP high definition of methylation of two or more of the CpG islands MINT 1, 2, 31 and CDKN2A (original panel minus hMLH1). As can be seen, the differences between CIMP high stable and unstable tumors are still present and, in addition, unstable CIMP high tumors show a significant trend towards older age.

CIMP and family history of cancer: There was a tendency for CIMP high stable tumors to have a positive family history of colorectal cancer, but this was not statistically significant (OR 1.59, 95% C.I. 0.91, 2.80). Individuals with CIMP high stable and CIMP high unstable tumors had very similar prevalences of reported family history of colorectal cancer (27.3% and 30.3%, respectively). Using a previously described methylation panel(9), we saw no relationship between CIMP high and a family history of colorectal cancer or of any other type of cancer.

BRAF and KRAS2: KRAS2 and BRAF mutations were nearly mutually exclusive. 494 of 859 (57.5%) cancers were wild type for both BRAF and KRAS2, 279 (32.5%) were mutant for KRAS2 and wild type for BRAF, and 85 (9.9%) were mutant for BRAF but wild type for KRAS2. Only one of 859 cancers (0.1%) had mutations in both genes.

Distribution of CpG island methylation in microsatellite stable and unstable tumors: A graph of the percent of tumors versus the number of CpG islands methylated per tumor for microsatellite stable and unstable tumors is shown in FIG. 2. There is a steady decrease in the number of microsatellite stable tumors with increasing numbers of methylated sites. In contrast, there is a suggestion of a bimodal distribution of CIMP amongst unstable tumors, with most unstable tumors exhibiting high degrees of methylation. In fact, this figure suggests that it may be appropriate to set a higher threshold for CIMP high than the 2 of 5 markers used in this and previous studies. Using a cut-off of 3 or more methylated markers for CIMP high led to stronger relationships in unstable tumors with KRAS2 wild type (OR 0.08, 95% C.I. 0.02, 0.47), increased stage (p=0.045), older age (p<0.0001), female gender (OR 3.07, 95% C.I. 1.12, 8.41), poor differentiation (p=0.0014), and the BRAF V600E mutation (OR 22.21 95% C.I. 4.69, 105.31) than previously seen in Table 3. Using these same criteria for stable tumors, however, weakened most of the relationships seen with CIMP in univariate and multivariate analyses.

Discussion: In this large, population-based study fairly low levels of C1MP in colon cancer in general (29.6% of 864 tumors) and in stable tumors (24.4% were observed. This is consistent with previous relatively large, unselected series of colorectal cancers but is less than the 50% originally reported. Unstable tumors, in contrast, were heavily methylated (82.1%) and this difference was statistically significant. hMLH1 methylation was seen in most unstable tumors regardless of the method used to measure this feature. However, it should be noted that the primers originally used for determination of hMLH1 methylation are also positive in 15.3% of stable tumors, most of which are CIMP low, findings consistent with previous studies. Therefore, hMLH1 methylation as determined by these primers does not necessarily indicate that a tumor is either microsatellite unstable or CIMP high. hMLH1 methylation as detected by the primers used by Park et al (see Methods above) were more specific for unstable tumors but somewhat less sensitive. In microsatellite stable tumors we observed significant univariate relationships between CIMP high and proximal tumor site, higher AJCC stage, mutant KRAS2, increased age, poor histologic differentiation, mucinous histology, and, especially, the BRAF V600E mutation. A trend was seen with wild type TP53, but this was not statistically significant. These relationships have been previously reported individually, but the large population-based study is the first to have reported all of these associations and is the largest study to date. A trend towards a positive family history of colorectal cancer in highly methylated stable tumors was seen, although this was not statically significant.

This study is the first to show the effect of multivariate analyses on the relationship between CIMP and clinicopathological variables in stable colon cancers. This is important because a recent study questioned the biologic relevance of CIMP and whether once unstable tumors were removed from the analysis any relationships other than older age and proximal location would be seen. The multivariate analyses convincingly show relationships between CIMP in stable tumors and clinicopathologic variables independent of site and age, including higher stage, KRAS2 mutations, a remarkably strong relationship with the BRAF V600E mutation and a trend towards poor differentiation.

As in previous studies, KRAS2 and BRAF mutations were nearly mutually exclusive, supporting their participation in the same signaling pathway. CIMP high microsatellite unstable tumors shared some features with CIMP high stable tumors, namely associations with proximal location, older age and, especially, the BRAF V600E mutation. Indeed, CIMP high unstable tumors were even more than their stable counterparts to be proximal and have the BRAF mutation (64.1% vs. 17.6%), and were also more likely to be TP53 wild type and poorly differentiated. CIMP high unstable tumors differed from their stable counterparts in their associations with lower rather than higher AJCC stage and wild type rather than mutant KRAS2. The similarities between CIMP high stable and unstable tumors, especially the excess BRAF mutations, support the general concept of a CIMP phenotype, while their differences highlight the effect of microsatellite instability on the expression of that phenotype.

The younger age, increased KRAS2 mutations, relative lack of BRAF mutations, and less proximal predominance of CIMP low unstable tumors all suggest that at least some of these CIMP low unstable tumors were from individuals with hereditary non-polyposis colon cancer (HNPCC). Using the higher threshold for CIMP high for unstable tumors shown herein (3 or more methylated markers), 23 of 81 unstable tumors are CIMP low. hMLH1 and hMSH2 mutations have previously been ruled out in a little more than half of these 23 individuals by sequencing. However, even in this group some contribution of relatively large deletions in these genes and/or mutations in other mismatch repair genes, such as hMSH6, may have occurred. There is some evidence, however, that there may be a contribution of sporadic unstable tumors to this CIMP low group (less than 3 methylated markers). First of all, although this group is significantly younger than the unstable CIMP high unstable tumors, 39% of these individuals were 65 years of age or older at the time of cancer diagnosis, ages which would be unusual for HNPCC. Also, 50% (8 of 16 with interview data) of these individuals did not have a family history of colorectal cancer. There is also some support in the literature for sporadic CIMP low unstable tumors. In a recent study approximately 40% of sporadic unstable tumors lacked hMLH1 methylation (similar to our percentage which lacked hMLH1 methylation by the primers used by Park et al). This suggests the possibility of a component of a non-HNPCC, non-CIMP high pathway to unstable colorectal cancer; studies with larger numbers of CIMP low unstable tumors will be necessary to verify this. At any rate, our results do support suggestions that the presence of CIMP high and/or BRAF mutations may be a clinically useful test to exclude the possibility of HNPCC in an individual with an unstable tumor.

As mentioned above, the concept of CIMP, especially in stable tumors, has recently been challenged. As in that report we did not observe an obvious bimodal distribution of the number of methylated markers in stable tumors in contrast to the situation with unstable tumors which, as stated above, may be due to at least partly to inclusion of some cases of HNPCC. Nevertheless, while the division of CIMP high and low may be somewhat arbitrary in stable tumors, at least as methylation was assessed in this study, it was observed that significant univariate and multivariate relationships between CIMP high and many clinicopathologic variables and tumor mutations in stable tumors.

These relationships to other biologic variables suggest that CIMP high in stable tumors is more than simply the high end of a normal distribution or, as suggested previously, a result of older age and/or proximal location of tumor. It is possible that there are better indicators of CIMP status which may lead to a more definite separation between CIMP high and low among stable tumors. It is also possible, as our data comparing clinicopathologic associations with different definitions of CIMP in unstable tumors suggest, that different definitions of CIMP may be appropriate for stable and unstable tumors. Another possible approach would be to eliminate hMLH1 methylation from the panel of CpG islands, as the rarity of hMLH1 methylation in stable tumors indicates that CIMP status in these tumors is mostly determined by the other four CpG islands.

In summary, in a large population-based study we have presented evidence for a CIMP high phenotype in both stable and unstable colon cancers. Most importantly, the multivariate analyses of CIMP high in stable tumors showed significant relationships to other clinicopathologic variables and tumor mutations, especially the BRAF V600E mutation, which were independent of proximal location and increased age. The similarities between CIMP high stable and unstable tumors, especially the excess BRAF mutations, support the general concept of a CIMP phenotype, while their differences highlight the effect of microsatellite instability on the expression of that phenotype.

G. REFERENCES

1. Davies H, Bignell G R, Cox C, et al. Mutations of the BRAF gene in human cancer. *Nature* 417:949-54 (2002).
2. Rajagopalan H, Bardelli A, Lengauer C, Kinzler K W, Vogelstein B, Velculescu V E. Tumorigenesis: RAF/RAS oncogenes and mismatch-repair status. *Nature* 418:934 (2002).
3. Wang L, Cunningham J M, Winters J L, et al. BRAF mutations in colon cancer are not likely attributable to defective DNA mismatch repair. *Cancer Res* 63: 5209-12 (2003).
4. Samowitz W S, Curtin K, Ma K N, et al. Microsatellite instability in sporadic colon cancer is associated with an improved prognosis at the population level. *Cancer Epidemiol Biomarkers Prev* 10:917-23 (2001).
5. Halling K C, French A J, McDonnell S K, et al. Microsatellite instability and 8p allelic imbalance in stage B2 and C colorectal cancers. *J Natl Cancer Inst* 91: 1295-303 (1999).
6. Toyota M, AhujaN, Ohe-Toyota M, Herman J G, Baylin S B, Issa J P. CpG island methylator phenotype in colorectal cancer. *Proc Natl Acad Sci USA* 96: 8681-6 (1999).
7. Toyota M, Ohe-Toyota M, Ahuj a N, Issa J P. Distinct genetic profiles in colorectal tumors with or without the CpG island methylator phenotype. *Proc Natl Acad Sci USA* 97:710-5 (2000).
8. Kambara T, Simms L A, Whitehall V L, et al. BRAF mutation is associated with DNA methylation in serrated polyps and cancers of the colorectum. *Gut* 53:1137-44 (2004).
9. Nagasaka T, Sasamoto H, Notohara K, et al. Colorectal cancer with mutation in BRAF, KRAS, and wild-type with respect to both oncogenes showing different patterns of DNA methylation. *J Clin Oncol* 22: 4584-94 (2004).
10. Slattery M L, Potter J, Caan B, et al. Energy balance and colon cancer—beyond physical activity. *Cancer Res* 57:75-80 (1997).
11. American Joint Committee on Cancer. AJCC Cancer Staging Manual. 5th ed. Philadelphia: Lippincott-Raven (1997).
12. Park S J, Rashid A, Lee J H, Kim S G, Hamilton S R, Wu T T. Frequent CpG island methylation in serrated adenomas of the colorectum. *Am J Pathol* 162: 815-22 (2003).
13. Frazier M L, Xi L, Zong J, et al. Association of the CpG island methylator phenotype with family history of cancer in patients with colorectal cancer. *Cancer Res* 63:4805-8 (2003).
14. Samowitz W S, Curtin K, Ma K N, et al. Prognostic significance of p53 mutations in colon cancer at the population level. *Int J Cancer* 99:597-602 (2002).
15. Samowitz W S, Curtin K, Schaffer D, Robertson M, Leppert M, Slattery M L. Relationship of Ki-ras mutations in colon cancers to tumor location, stage, and survival: a population-based study. *Cancer Epidemiol Biomarkers Prev* 9:1193-7 (2000).

16. Samowitz W S, Holden J A, Curtin K, et al. Inverse relationship between microsatellite instability and K-ras and p53 gene alterations in colon cancer. *Am J Pathol* 158:1517-24 (2001).
17. van Rijnsoever M, Grieu F, Elsaleh H, Joseph D, Iacopetta B. Characterisation of colorectal cancers showing hypermethylation at multiple CpG islands. *Gut* 51:797-802 (2002).
18. Hawkins N, Norrie M, Cheong K, et al. CpG island methylation in sporadic colorectal cancers and its relationship to microsatellite instability. *Gastroenterology* 122:1376-87 (2002).
19. Young J, Barker M A, Simms L A, et al. Evidence for BRAF mutation and variable levels of microsatellite instability in a syndrome of familial colorectal cancer. *Clin Gastroenterol Hepatol* 3:254-63 (2005).
20. Ward R L, Williams R, Law M, Hawkins N J. The CpG island methylator phenotype is not associated with a personal or family history of cancer. *Cancer Res* 64:7618-21 (2004).
21. Wan P T, Garnett M J, Roe S M, et al. Mechanism of activation of the RAF-ERK signaling pathway by oncogenic mutations of B-RAF. *Cell* 116:855-67 (2004).

What is claimed is:

1. A method of prognosing survival rates in a human subject diagnosed with a stage II colon cancer, comprising: a) amplifying via PCR a nucleic acid sample obtained from a tumor isolated from the subject and detecting amplification of a microsatellite panel comprising BAT26 and TGFBRII with agents that specifically identify said microsatellite panel members to measure microsatellite stability; b) assaying a tumor sample isolated from the human subject to detect the presence of a BRAF mutation in the sample, wherein the BRAF mutation is determined using a forward primer and a reverse primer; and wherein the forward primer is 5'-TCATAATGCTTGCTCTGATAGGA (SEQ ID NO: 1) and the reverse primer is 3'-CTTTCTAGTAACTCA- GCAGC (SEQ ID NO: 2); and wherein the BRAF mutation comprises V600E; and c) prognosing a decreased survival rate of the subject diagnosed with stage II colon cancer by determining the presence of microsatellite stability and a presence of a BRAF mutation in steps a) and b).

2. The method of claim 1, wherein the survival rate is measured by American Joint Committee on Cancer stage designation.

3. The method of claim 1, wherein the survival rate is measured by the percentage of chance for five-year survival.

4. The method of claim 3, wherein the chance of survival is greater than 10%.

5. The method of claim 3, wherein the chance of survival is greater than 20%.

6. A method of classifying severity of colon cancer in a human subject diagnosed with a stage II disease, comprising a) amplifying via PCR a nucleic acid sample obtained from a tumor isolated from the subject and detecting amplification of a microsatellite panel comprising BAT26 and TGFBRII with agents that specifically identify said microsatellite panel members to measure microsatellite stability; b) assaying a tumor sample isolated from the subject to determine the presence of a BRAF mutation in the sample, wherein the BRAF mutation is determined using a forward primer and a reverse primer; and wherein the forward primer is 5'-TCATAATGCTTGCTCTGATAGGA (SEQ ID NO: 1) and the reverse primer is 3'-CTTTCTAGTAACTCA-GCAGC (SEQ ID NO: 2); and wherein the BRAF mutation comprises V600E; and c) classifying the colon cancer as aggressive in subjects having stage II colon cancer expressing microsatellite stability and a BRAF mutation when compared to tumor samples expressing microsatellite stability and wild type BRAF.

* * * * *

```
                              SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 1
tcataatgct tgctctgata gga                                                23

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 2
ctttctagta actcagcagc                                                    20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 3
tcataatgct tgctctgata gga                                                23

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 4
ctttctagta actcagcagc                                                    20
```